(12) United States Patent
Isacson et al.

US008153422B2

(10) Patent No.: US 8,153,422 B2
(45) Date of Patent: Apr. 10, 2012

(54) DOPAMINERGIC NEURONS DIFFERENTIATED FROM EMBRYONIC CELLS FOR TREATING NEURODEGENERATIVE DISEASES

(75) Inventors: Ole Isacson, Belmont, MA (US); Lars Bjorklund, Stockholm (SE)

(73) Assignee: The McLean Hospital Corporation, Belmont, MA (US)

( * ) Notice: Subject to any disclaimer, the term of this patent is extended or adjusted under 35 U.S.C. 154(b) by 339 days.

(21) Appl. No.: 12/107,725

(22) Filed: Apr. 22, 2008

(65) Prior Publication Data

US 2008/0274548 A1 Nov. 6, 2008

Related U.S. Application Data

(63) Continuation of application No. 10/731,550, filed on Dec. 9, 2003, now abandoned.

(60) Provisional application No. 60/432,128, filed on Dec. 9, 2002.

(51) Int. Cl.
*C12N 15/85* (2006.01)
*C07H 21/04* (2006.01)
*C07H 21/02* (2006.01)
*A61K 48/00* (2006.01)
*C07K 16/00* (2006.01)

(52) U.S. Cl. ...... 435/325; 435/455; 536/23.1; 536/24.5; 514/44; 530/387.1

(58) Field of Classification Search ............... 435/91.31, 435/69.1, 455; 536/23.1, 24.5, 23.5
See application file for complete search history.

(56) References Cited

U.S. PATENT DOCUMENTS

| 5,981,165 | A | 11/1999 | Weiss et al. |
| 6,277,820 | B1 | 8/2001 | Rosenthal et al. |
| 6,284,539 | B1 | 9/2001 | Bowen et al. |
| 6,395,546 | B1 | 5/2002 | Zobel et al. |
| 2002/0076799 | A1 | 6/2002 | Wang |
| 2002/0098582 | A1 | 7/2002 | Gold et al. |
| 2002/0127715 | A1 | 9/2002 | Benvenisty et al. |
| 2002/0146678 | A1 | 10/2002 | Benvenisty |
| 2002/0164791 | A1* | 11/2002 | Van Der Kooy et al. ..... 435/366 |
| 2003/0103959 | A1* | 6/2003 | Hughes et al. ............. 424/94.63 |

FOREIGN PATENT DOCUMENTS

| WO | WO 94/09119 | 4/1994 |
| WO | WO 94/10292 | 5/1994 |
| WO | WO 94/16718 | 8/1994 |

OTHER PUBLICATIONS

Wagner et al, Nature Biotech., vol. 17, pp. 653-659 (1999).*
Moore et al., Extol. Neurology, vol. 172, pp. 363-376 (2001).*
Chirila et al., Biomaterials, vol. 23, pp. 321-342 (2002).*
Agrawal et al., Molecular Med. Today, vol. 6, pp. 72-81 (2000).*
Opalinska et al., Nature Rev., vol. 1, pp. 503-514 (2002).*
Jang et al., Expert Rev. Medical Devices, vol. 1, No. 1, pp. 127-138 (2004).*
Chambers et al., Nat Biotechnol, 27(3):275-280 2009.
International Search Report dated Jan. 13, 2005 for PCT Application No. PCT/US03/389.
Lonardo et al., Stem Cells, 28:1326-1337, 2010.
Notice of Panel Decision from Pre-Appeal Brief Review dated Nov. 23, 2007 for U.S. Appl. No. 10/731,550.
Parish et al., Stem Cells, 23:471-476, 2005.
Patani et al., PLOS One, 4(10):e7327, 2009.
Qin et al., Structure, 7(1):1493-1503, 1999.
Shi et al., Nature, 388(6637):87-93, 1997.
US Office Action dated Jul. 12, 2007 for U.S. Appl. No. 10/731,550.
US Office Action dated Oct. 2, 2006 for U.S. Appl. No. 10/731,550.
US Office Action dated Jan. 31, 2007 for U.S. Appl. No. 10/731,550.
Abuin et al., "Full speed mammalian genetics: in vivo target validation in the drug discovery process" Trends in Biotechnol. 20:36-42 (2002).
Attisano et al., "Signal Transduction by the TGB-β superfamily" Science 296.: 1646-1647 (2002).
Björklund et al. "Embroyonic Stem Cells Develop Into Functional Dopaminergic Neurons after Transplantation in a Parkinson rat model" Proc. Natl. Acad. Sci. USA 99: 2344-2349 (2002).
Bronson et al. "Altering mice by homologous recombination using embryonic stem cells" J Biol. Chem. 269: 27155-27158 (1994).
Brustle et al. "Embryonic stem cell-derived glial precursors: a source of myelinating transplants" Science 285: 754-756 (1999).
Cazorla et al. "A Response Element for the Homeodomain Transcription Factor Ptx3 in the Tyrosine Hydroxylase Gene Promoter." J. of Neurochem. 74: 1829-1837 (2000).
Deacon et al. "Blastula-stage Stem Cells can Differentiate into Dopaminergic and Serotonergic Neurons after Transplantation." Experimental Neurology 149: 28-41 (1998).
Eiges et al. "Establishment of Human Embryonic Stem Cell-transfected Clones Carrying a Marker for Undifferentiated Cells" Current Biology 11:514-518 (2001).
Flax et al. "Engraftable Human Neural Stem Cells Respond to Developmental Cues, Replace Neurons, and Express Foreign Genes" Nature Biotechnology 16: 1033-1039 (1998).
Friedmann, "Overcoming the Obstacles to Gene Therapy" Scientific American 96-101 (Jun. 1997).
Hemmati-Brivanlou et al. "Vertebrae Embryonic Cells will become Nerve Cells unless told Otherwise" Cell 88: 13-17 (1997).
Hynes et al. "Embryonic Stem Cells go Dopaminergic" Neuron 28:11-14 (2000).

(Continued)

*Primary Examiner* — Amy Bowman
(74) *Attorney, Agent, or Firm* — Foley & Lardner LLP

(57) ABSTRACT

Disclosed herein are methods for generating dopaminergic neurons in vitro by inhibiting a pathway component of a TGF-β signaling pathway and overexpressing one or more cell fate-inducing polypeptides in pluripotent cells, causing differentiation of the pluripotent cells into dopaminergic neurons. Also disclosed are methods for treating a neurodegenerative disease in a patient by generating dopaminergic neurons in vitro, and transplanting them into the brain of the patient, such that the dopaminergic neurons are sufficient to reduce or eliminate the symptoms of the neurodegenerative disease.

12 Claims, 6 Drawing Sheets

OTHER PUBLICATIONS

Isacson et al. "Parkinson's Disease: Interpretations of Transplantation Study are Erroneous" Nature Neuroscience 4:553 (Jun. 2001).
Jackowski. "Neural Injury Repair: Hope for the Future as Barriers to Effective CNS Regeneration become clearer" British Journal of Neurosurgery 9: 303-317 (1995).
Jordan et al. "Bone Morphogenetic Proteins: Neurotrophic Roles for Midbrain Dopaminergic Neurons and Implications of Astroglial cells" Eur. J. Neuroscience 9:1699-1710 (1997).
Kalderon. "Transducing the Hedgehog Signal" Cell 103:371-374 (2000).
Kawasaki et al. "Induction of Midbrain Dopaminergic Neurons from ES cells by Stromal Cell-Derived Inducing Activity" Neuron 28: 31-40 (2000).
Kim et al. "Dopamine Neuron Derived from Embryonic Stem Cells Function in an Animal Model of Parkinson's Disease" advanced online publication Nature (Jun. 20, 2002) (doi:1038/nature00900).
Krieglstein et al. "Development of Mesencephalic Dopaminergic Neurons and the Transforing Growth factor-β Superfamily" J. Neural Transm 46 (Suppl): 209-216 (1995).
Krieglstein et al. "TGF-β and the regulation of Neuron Survival and Death" J Physiology 96: 25-30 (2002).
Lee et al. "Efficient Generation of Midbrain and Hindbrain Neurons from Mouse Embryonic Stem Cells" Nat. Biotechnol. 18: 675-679 (2000).
Li et al. "Generation of Purified Neural Precursors from Embryonic Stem Cells by Lineage Selection" Curr. Biol. 8: 971-974 (1998).
Lim et al. "Noggin Antagonizes BMP Signaling to Create a Niche for Adult Neurogenesis" Neuron 28: 713-728 (2000).
Lindvall. :Engineering Neurons for Parkinson's Disease Nature Biotechnology 17:635-363 (1999).
McDonald et al. :Transplanted Embryonic Stem Cells Survive, Differentiate and Promote Recovery in Injured Rat Spinal Cord: 5: 1410-1412 (1999).
McMahon. "More Surprises in the Hedgehog Signaling Pathway" Cell 100: 185-188 (2000).
Minchiotti et al. "Role of EGF-CFC Gene Cripto Cell Differentiation and Embryo Development" Gene 287: 33-37 (2002).
Orkin and Motulsky. "Report and Recommendations of the Panel to Assess the NIH Investment in Research on Gene Therapy" (Dec. 1995).
Odorico et al. "Multilineage Differentiation from Human Embryonic Stem Cell Lines" Stem Cells 19: 193-204 (2001).
Piccini et al. "Delayed Recovery of Movement-related Cortical function in Parkinson's Disease after Striatal Dopaminergic Grafts" Annals of Neurology 48: 689-695 (2000).
Piccini et al. "Dopamine Release from Nigral Transplants Visualized in vivo in a Parkinson's Patient" Nature Neuroscience 2:1137-1140 (1999).
Reynold and Weiss. :Generation of Neurons and Astrocytes from Isolated Cells of the Adult Mammalian Central Nervous System Science 255: 1707-1710 (1992).
Stull et al. Induction of a Dopaminergic Phenotype in Cultured Striatal Neurons by Bone Morphogenetic Proteins: Developmental Brain Research 130: 91-98 (2001).
Tiedemann et al. "Pluripotent Cells (Stem Cells) and their Determination and Differentiation in early Vertebrae Embryogenesis" Develop. Growth Differ. 43: 469-502 (2001).
Tropepe et al. "Direct Neural Fate Specification from Embryonic Stem Cells: a Primitive Mammalian Neural Stem Cell Stage Acquired through a Default Mechanism" Neuron 30: 65-78 (2001).
Verma and Somia. Gene Therapy—Promises, Problems and Prospects: Nature 389: 239-242 (1997).
Wagner et al. "Induction of a Midbrain Dopaminergic Phenotype in Nurr1—overexpressing Neural Stem Cells by type 1 Astrocytes" Nat. Biotechnol. 17: 653-659 (1999).
Zwaka et al. :Homologous Recombination in Human Embryonic Stem Cells Nature Biotechnology, advanced online publication, pp. 1-3. (Feb. 10, 2003).
Sakurada et al. "Nurr1, an Orphan Nuclear Receptor, is a Transcriptional Activator of Endogenous Tyrosine Hydroxylase in a Neural Progenitor Cells Derived from the Adult Brain" Development, vol. 126: 4017-4026 (1999).
Ramsden et al. "The Aetiology of Idiopathic Parkinson's Disease" Journal of Clinical Pathology: Molecular Pathology; vol. 54: 369-380 (2001).
Opalinska et al., Nature Rev. vol. 1: 503-514 (2002).
Crooke., Antisense Res. & Application, Chapter 1, pp. 1-50 (Ed. S.T. Crooke. Publ. Springer-Velag) (1998).
Chirila et al., Biomaterials, vol. 23: 321-342 (2002).
Perachhi., Rev. Med. Virol., vol. 14: 47-64 (2004).
Agrawal et al., Molecular Med. Today, vol. 6: 72-81 (2000).
Branch., Trends in Biochem. Sci., vol. 23: 45-50 (1998).
Zhao et al. "Abrogation of Smad3 and Smad2 or of Smad4 Gene Expression Positively Regulates Murine Embryonic Lung Branching Morphogenesis in Culture" Developmental Biology 194:182-195 (1998).
Kretschmer et al. "Differential Regulation of TGF-β signaling through Smad2, Smad3, and Smad4" Oncogene 22: 6748-6763 (2003).
Zhang et al. "Adenovirus-Mediated Gene Transfer of Dominant-Negative Smad4 Blocks TGF-β Signaling in Pancreatic Acinar Cells" Am J Physiol Gastrointest Liver Physiol 280: G1247-G1253 (2001).
Chen et al. :Smad4/DPC4-dependent Regulation of Biglycan Gene Expression by Transforming Growth Factor-β in Pancreatic Tumor Cells The Journal of Biological Chemistry, vol. 277, No. 39, Issue of Sep. 27: 36118-36128 (2002).
Simeone et al. "Smad4 Mediates Activation of Mitogen-Activated Protein Kinases by TGF-β in Pancreatic Acinar Cells" Am J Physiol Cell Physiol 281: C311-C319 (2001).

* cited by examiner

FIGURE 1

| DVR Subfamily | TGFβ Subfamily | Activin/Inhibin Subfamily | GDNF Subfamily | Distant Members |
|---|---|---|---|---|
| Nodal<br>Xenopus laevis nodal related [Xnr] 1-3<br>BMP2, 3, 3b, 4, 5, 6, 7, 8, 8b, 9, 10, 11, 15<br>dpp-c<br>GDF1, 2, 3, 5, 6, 7, 8, 9, 9b, 10, 11<br>60A<br>derriere<br>Vg1<br>OP1, 2<br>Dpp<br>Vgr1 | TGFβ1<br>TGFβ2<br>TGFβ3<br>TGFβ4<br>TGFβ5 | Activin βA<br>Activin βB<br>Activin βC<br>Activin βD<br>Activin βE<br>Inhibin α | Artemin<br>GDNF<br>Neurturin<br>Persephin | Müllerian inhibiting substance (MIS), or anti-Müllerian hormone (AMH)<br>GDF15<br>Lefty1, 2 |

SEQUENCE LISTING

```
<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ggtgatgacc tggccgtcag gcagctcgta                                        30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
aaccccaagg ccaaccgcga gaagatgacc                                        30

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
catggacctc accaacactg                                                   20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gagacaggtg tcttcctctg                                                   20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tcctgcactc cctgtcagag                                                   20

<210> SEQ ID NO 6
<211> LENGTH: 21
<212> TYPE: DNA
<213> ORGANISM: Artificial Sequence
```

```
<220> FEATURE:
<223> OTHER INFORMATION: Primer

<400> SEQUENCE: 6
ccaagagcag cccatcaaag g                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gagcatcaca cagggttctg                                                20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cacctttaaa tcgcgctcct c                                              21

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
acaattcatc tgcttgtctg tcc                                            23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
cggttgttac aagtctcagc ac                                             22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gaggtccatg gtgtttaagg ac                                             22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ctgcagcagg ttgtcaatct tgg                                            23
```

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
agatgcgccc catcaagaca g                                                 21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ccggaacacc catatcctaa g                                                 21

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
aactatgtag gggactcaga cctgc                                             25

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tctcacactc tttccgcacg ac                                                22

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gaggtgacca agccactctc c                                                 21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
agggttagga cactcgccct c                                                 21

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19

```
gcaactgtga acatgatgtt cg                                              22

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tgaggtcctg gtccatcacg                                                 20
```

DOPAMINERGIC NEURONS DIFFERENTIATED FROM EMBRYONIC CELLS FOR TREATING NEURODEGENERATIVE DISEASES

This application is a continuation of U.S. application Ser. No. 10/731,550, filed Dec. 9, 2003, which claims benefit of U.S. Provisional Application No. 60/432,128, filed Dec. 9, 2002, each of which is hereby incorporated by reference.

STATEMENT OF GOVERNMENT SPONSORED RESEARCH

This invention was made with government support under Grant No. NS39793 awarded by the National Institutes of Health. The government has certain rights in the invention.

BACKGROUND OF THE INVENTION

Neurodegenerative disorders such as Parkinson's, Alzheimer's, and Huntington's disease are becoming ever more prominent in our society. A direct approach towards therapeutic treatment of these diseases is through replacement therapy where undamaged tissue is transplanted into the nervous system. Recently, significant progress has been achieved with transplants in Parkinson's disease (PD), but the process is heavily dependent on an unstable and problematic source of fetal tissue. Embryonic stem (ES) cells may be a tissue/cell source for developing the therapeutic potential of neural transplantation. Self-renewing and multipotent stem cells provide a source of transplantable material to replace post-mitotic neurons that do not spontaneously regenerate after injury.

PD is a progressive neurodegenerative disease characterized clinically by bradykinesia, rigidity, and resting tremor. The motor abnormalities are associated with a specific loss of dopaminergic neurons in the substantia nigra pars compacta (SNc) and depletion of striatal dopamine (DA) levels. While the loss of striatal DA correlates with the severity of clinical disability, clinical manifestations of PD are not apparent until about 80-85% of SNc neurons have degenerated and striatal DA levels are depleted by about 60-80%. DA neurons in the ventral midbrain consist of two main groups: the A9 group in the SN, and the A10 group in the ventral and ventral tegmentum. Each of these cell groups project to different anatomical structures and is involved in distinct functions. A9 cells mainly project to the dorsolateral striatum, involved in the control of motor functions, whereas A10 cells provide connections to the ventromedial striatum, limbic and cortical regions, involved in reward and emotional behavior. In addition to the distinct axonal projections and differences in synaptic connectivity, these groups of DA cells exhibit differences in neurochemistry and electrophysiological properties, illustrating functional differences despite similar neurotransmitter identity. These differences in A9 and A10 cells are also reflected in their specific responses to neurodegeneration in PD. Postmortem analyses in human PD brains demonstrate a selective cell loss of the A9 group with a survival rate of about 10% whereas the A10 group is largely spared with a survival rate of about 60%. This indicates that A9 cells are more vulnerable to intrinsic and/or extrinsic factors causing degeneration in PD. In addition, three regional gradients of neurodegeneration in the dorso-ventral/rostro-caudal/medio-lateral axis have been reported in PD. Caudally and laterally located ventral DA cells within A9 subgroups are the most vulnerable cells in PD. In contrast, the medial and rostral part of DA cell subgroups within A10 cells (i.e. rostral linear nucleus, RLi) are the least affected (5-25% cell loss).

Current clinical data indicate proof of principle for cell implantation as a therapy for PD. It has recently been shown that ES cells, when transplanted in low numbers into the striatum, develop into fully-differentiated DA neurons that can restore cerebral function and behavior in an animal model of PD (Björklund et al., *Proc. Natl. Acad. Sci. USA* 99:2344-2349, 2002). Furthermore, the PD process does not appear to negatively affect the transplanted cells; however, the endogenous DA neurons continue to degenerate. The stem cells may themselves be transplanted or, alternatively, they may be induced to produce differentiated cells (e.g., neurons, oligodendrocytes, Schwann cells, or astrocytes) for transplantation.

Differentiation of stem cells into various cell types is regulated by a host of intracellular and extracellular factors. For example, the transforming growth factor-$\beta$ (TGF-$\beta$) superfamily of secreted polypeptide factors regulates a variety of homeostatic and developmental processes, including stem cell determination and differentiation during embryogenesis. A basic understanding of the signal transduction pathway from the TGF-$\beta$ signal to the target genes that generate the biological responses has been worked out (Attisano et al., *Science* 296:1646-1647, 2002). Binding of a TGF-$\beta$ member to an appropriate cell-surface receptor leads to phosphorylation of intracellular protein mediators called Smads, in particular the class of Smads known as the R-Smads, which then accumulate in the nucleus as heteromeric complexes with a second class of Smads, the Co-Smads (of which Smad4 is the only known mammalian example at this time). In the nucleus, the R-Smad/Co-Smad complexes associate with particular transcriptional coactivators or corepressors, thereby differentially affecting gene expression and generating diverse biological responses. Inhibitory Smads, or I-Smads (e.g., Smad6 and -7), which antagonize TGF-$\beta$ signaling, are also known.

Included in the TGF-$\beta$ superfamily are nodal, bone morphogenic proteins (BMPs), and activins. Mice homozygous for a mutation of the nodal gene fail to form the primitive streak and most of the mesoderm. Pathway for transducing the nodal signal involves activin receptor-like kinase receptors (e.g., ALK4 and ALK7) and SMADs (e.g., Smad2), and is regulated by members of the ECF-CFC family (e.g., Cryptic, Oep (from zebrafish), and Cripto). Similarly, activins, which induce mesodermal tissues and endoderm, operate through signal transduction pathways that involve receptors (e.g., activin receptor I, activin receptor II, activin receptor IIb, TGF-$\beta$ receptor, ALK4, and ALK7) and SMADs (e.g., smad2, smad3, and smad4). Related to activin, BMP (e.g., BMP2, BMP4, and BMP7) utilizes signal transduction pathways that involve BMP receptors (BMPR) and activin receptors (e.g., BMPRIa, BMPRIb, BMPRII, ALK1, ALK2, ALK3, and ALK6), and SMAD proteins (e.g., Smad4, Smad5, and Smad6).

SUMMARY OF THE INVENTION

The invention generally provides a method for generating dopaminergic neurons in vitro by inhibiting one or more pathway components of a TGF-$\beta$ signaling pathway in pluripotent cells that overexpress one or more cell fate-inducing polypeptides. The invention also provides methods and compositions for treating a neurodegenerative disease in a patient by transplanting these dopaminergic neurons into the brain of the patient, such that the transplanted dopaminergic neurons are sufficient to reduce or eliminate the symptoms of the neurodegenerative disease.

The cell fate-inducing polypeptide can be overexpressed by providing a polynucleotide encoding the cell fate-inducing polypeptide operably linked to a promoter and introducing the polynucleotide into the pluripotent cells under conditions suitable for expressing the polynucleotide.

In a particularly useful embodiment, the cell fate-inducing polypeptide is any one of Nurr-1, PTX3, Shh, AP-2, Phox2a, or Phox2a1. However, pluripotent cells may be directed along a dopaminergic lineage by expressing two, three, four, or more cell fate-inducing polypeptides. In another particularly useful embodiment, both Nurr-1 and PTX3 are overexpressed. Preferably, the neurodegenerative disease is PD or another neurodegenerative disease characterized by the loss of DA neurons. The DA neurons produced by the methods of the invention may be transplanted into any region of the nervous system that will result in a reduction or elimination of some or all of the symptoms of the disease being treated. Preferably, the DA neurons are transplanted into the substantia nigra (SN), ventral tegmental area (VTA), caudate, putamen, hippocampus, nucleus accumbens, amygdala, thalamus, or any region of the cerebral cortex (e.g., the motor cortex, premotor cortex, frontal and prefrontal areas). The pluripotent cells can be embryonic stem cells, cord blood cells, bone marrow-derived stem cells, neural stem cells, placental stem cells, or pluripotent cells isolated from the amniotic fluid. The pluripotent cells can be of human, mouse, rat, porcine, or non-human primate origin. The transplanted cells that differentiate into DA neurons may express any dopaminergic phenotype but preferably have an A9 or A10 dopaminergic phenotype.

In one embodiment, the inhibited TGF-β signaling pathway is the Nodal signaling pathway. Preferably, the pathway component that is inhibited is Nodal, Cripto, Cryptic, ALK-4, ALK-7, or Smad2. More preferably, the pathway component is Cripto.

In another embodiment, the inhibited TGF-β signaling pathway is the Activin signaling pathway. The pathway component that is inhibited is preferably Activin, Activin receptor I, Activin receptor II, Activin receptor IIb, TGF-β receptor, ALK-4, ALK-7, Smad2, Smad3, or Smad4.

In another embodiment, the inhibited TGF-β signaling pathway is the BMP2, BMP4, or BMP7 signaling pathway. Preferably, the pathway component that is inhibited is BMP2, BMP4, BMP7, BMPRIa, BMPRIb, BMPRII, ALK-1, ALK-2, ALK-3, ALK-6, Smad4, Smad5, or Smad6.

Inhibition of a pathway component may be by any effective means but may involve any of the following strategies: structurally disrupting the nucleic acid encoding the pathway component in the pluripotent cells by gene knockout of the nucleic acid encoding the signaling pathway component; overexpressing in the pluripotent cells small interfering RNA complementary to the RNA encoding the signaling pathway component; overexpressing in the pluripotent cells antisense oligonucleotide of the nucleic acid encoding the signaling pathway component; overexpressing in the pluripotent cells antibodies specific to the signaling pathway component; contacting the pluripotent cells with antibodies specific to the signaling pathway component; and overexpressing in the pluripotent cells a dominant negative version of the signaling pathway component.

In another aspect, the invention also provides a mammalian (e.g., human) pluripotent cell (e.g., an embryonic stem cell or a neural stem cell) that overexpresses one or more cell fate-inducing genes and has a functional disruption of a TGF-β signaling pathway component. In desirable embodiments, one of the cell fate-inducing gene is Nurr-1 or PTX-3. In other desirable embodiments, the functional disruption may result from a homozygous deletion, a partial deletion, a missense mutation, or a point mutation in a gene encoding a TGF-β signaling pathway component. As above, any TGF-β signaling pathway component is suitable for disruption; however, disruptions in Nodal, Cryptic, Cripto, Activin, Activin receptor I, Activin receptor II, Activin receptor IIb, TGF-β receptor, ALK-1, ALK-2, ALK-3, ALK-4, ALK-6, ALK-7, BMP2, BMP4, BMP7, BMPRIa, BMPRIb, BMPRII, Smad2, Smad3, Smad4, Smad5, and Smad6 are particularly useful.

By "dopaminergic neuron" is meant a dopamine-producing neuron that expresses tyrosine hydroxylase (TH), neuron-specific enolase (NSE), 1-aromatic amino acid decarboxylase, vesicular monoamine transporter 2, dopamine transporter, Nurr-1, and dopamine-2 receptor ($D_2$ Receptor).

By "A9 dopaminergic neuron" or "A9 DA neuron" is meant a dopaminergic neuron that expresses retinaldehyde-1 (RALDH1; also known as aldehyde dehydrogenase-2 (ADH2) and GIRK2, in addition to the markers that are expressed by a dopaminergic neuron.

By "A10 dopaminergic neuron" or "A10 DA neuron" is meant a dopaminergic neuron that expresses, in addition to the polypeptides that are expressed by a dopaminergic neuron, calbindin D28K but not RALDH1/AHD2.

By "pluripotent cell" is meant any cell that can give rise to a neuronal cell, preferably, a dopaminergic neuron. Useful pluripotent cells include, for example, embryonic stem cells, cord blood cells, bone marrow-derived stem cells, neural stem cells, placental stem cells, and pluripotent cells isolated from the amniotic fluid.

By "embryonic stem cell" is meant a cell derived from a blastocyst which has the ability to divide and give rise to cells derived from the mesoderm, the endoderm, and the ectoderm. "Embryonic stem cell" is also meant to include embryoid body stem cells which are small aggregates that embryonic stem cells form when cultured ex vivo.

By "cell fate-inducing polypeptide" is meant a polypeptide that causes pluripotent cells to differentiate into cell types which normally reside within the nervous system, e.g., neurons or glia. Pluripotent cells may be induced to differentiate into a desired cell type by transfecting the cells with cell fate-inducing genes. These cell fate-inducing genes encode cell fate-inducing polypeptides, i.e., polypeptides that regulate cell fate decisions (e.g., transcription factors such as Nurr-1, PTX3, Phox2a, AP2, and Shh). Nurr-1 is known to regulate the development of midbrain dopaminergic neurons (Zetterstrom et al., *Science* 276: 248-250, 1997). Our studies further indicated that Nurr-1 may control dopaminergic fate by directly transactivating TH gene transcription. PTX3 is another transcription factor expressed in dopaminergic neurons that has a role in regulating TH expression (Cazorla et al., *J. Neurochem.* 74:1829-1837, 2000). Recent studies have showed that Phox2a is critical for both the development and neurotransmitter identity of noradrenergic neurons (Morin et al., *Neuron* 18: 411-423, 1997; Yang et al., *J. Neurochem.* 71:1813-1826, 1998). Shh is a signaling molecule which has been shown to be critical for determining the development of both the dopaminergic and serotonergic neurons (Ye et al., *Cell* 93:755-766, 1998). Our recent analysis also indicated that AP2 may control both the TH and dopamine β-hydroxylase promoter activities and thus regulate catecholamine production. Details of the cell-fate inducing genes and polypeptides can be accessed online using the PubMed database at The National Center for Biotechnology Information (NCBI); see below for Genebank Accession Numbers.

| Cell-fate inducing gene | Genebank accession number |
| --- | --- |
| Shh (human) | NM 000193 |
| AP-2 (human) | X77343 |
| Phox2a (human) | NM 003924 |
| Phox2a1 (human) | NM 005169 |
| PTX3 (Rat) | AJ011005 |
| PTX3 (human) | X6306 |
| Nurr-1 (human) | AB017586 |
| Nurr-1 (Rat) | U72345 |
| Nurr-2 (Mouse) | ABO14889 |

By "TGF-β family member" is meant a polypeptide that belongs to the TGF-β superfamily. Members share a conserved cysteine pattern, with the seven conserved cysteine residues giving rise to a structural feature called cystine knot motif. The TGF-β superfamily includes, but is not limited to, TGF-β1, TGF-β2, TGF-β3, TGF-4, TGF-β5. BMPs (BMP2, BMP4, BMP7), growth differentiation factors (GDFs), nodal, nodal-related (Xnr) 1-3, decapentaplegic (dpp), derriere, Vg1, vegetal-1-related, activins, inhibins, glial cell line-derived neurotrophic factor (GDNF), neurturin, artemin, persephin, Mullerian inhibiting substance (MIS, or anti-Mullerian hormone, AMH), and lefty1 and 2. These polypeptides are described in detail in Krieglstein et al., *J. Physiol.* 96:25-30, 2002; Massague, *Annu. Rev. Biochem.* 67:753-791, 1998; and references therein. FIG. 1 shows representative members of the TGF-β superfamily.

By "nodal" is meant the polypeptide whose amino acid sequence is specified in GenBank accession no. 20271343, or the polypeptide nodal that has been designated as member of the TGF-β superfamily, or a homolog thereof. Nodal and nodal-related polypeptides function as mesoderm inducers during gastrulation.

By "activin" is meant any one of the activins that belong to the TGF-β superfamily, or a homolog thereof. Activins are formed by homo-or heterodimerization of any of the activin β (referred to in some of the literature as inhibin β) subunits (A to E).

By "signaling pathway component" is meant any organic molecule that is involved in the signaling pathway of a TGF-β superfamily member, including the original TGF-β superfamily member ligand that binds to the receptor, that leads to endoderm and/or mesoderm differentiation. FIG. 2 outlines the basic events in the signaling pathway of a TGF-β signaling pathway and the various signaling pathway components involved.

By "overexpressing" is meant to effect an increase in the level of activity (for example, total activity of a cell fate-inducing polypeptide) by at least 20%, preferably by at least 50%, and more preferably by at least 75% or greater relative to the level in a control cell. Increase in activity levels may be accomplished by employing standard methods which are known in the art including, without limitation, administration of exogenous protein, and introduction of gene constructs containing a polynucleotide encoding the target protein or gene product. Levels of polypeptide or transcript are monitored according to any standard technique including, but not limited to, reverse transcriptase-PCR (RT-PCR), and immunoblotting.

By "administering" is meant the application, directly or indirectly, of a particular substance. For example, "administering an antisense RNA" would include not only administering antisense RNA but also administering DNA that encodes the antisense RNA. No particular limitation on the form or manner of introducing the substance is implied by the use of the term "administering".

By "gene knockout" is meant structural disruption of a gene or a nucleic acid encoding a polypeptide, leading to functional inactivation of the gene or nucleic acid. A gene knockout may be created by introducing a mutation (e.g., missense mutation, nonsense mutation, substitution mutation, deletion mutation, or insertion mutation) to an open reading frame, such that the open reading frame, which originally encoded for a particular functional product (protein or RNA), no longer encodes for that particular functional product. In one example, the mutation introduced creates a stop codon early in the open reading frame, resulting in the reading frame encoding for a truncated, and non-functional, gene product. Alternatively, the mutation introduced may alter the identity of a single amino acid in the encoded polypeptide, which amino acid is critical to the activity of the polypeptide, such that the encoded polypeptide is rendered inactive. Methods for gene knockout are well-known in the art (see, for example, U.S. Pat. Nos. 5,487,992 and 6,365,796). Structural disruption of the gene may be accomplished by homologous recombination using nucleic acids with substantial homology to the nucleic acid to be disrupted and at the same time carrying substitution, deletion, or insertion mutations. Preferably, gene knockout is performed using markers for positive or negative selection, to facilitate identification of cell lineages with the desired disruption.

By "inhibit" is meant to effect a reduction in the level of activity or expression of a target protein by at least 20%, preferably by at least 50%, and more preferably by at least 75% or greater relative to the level in a control cell. Reduction of activity levels may be accomplished by employing standard methods which are known in the art including, without limitation, overexpression of antisense oligonucleotides, short inhibitory RNA or dsRNA used for RNA interference, inhibitory antibodies, and dominant negative protein variants or gene products, and gene knockout technology. Levels of polypeptide or transcript are monitored according to any standard technique including, but not limited to, reverse trascriptase-PCR (RT-PCR), and immunoblotting.

By "antisense oligonucleotide" is meant a nucleic acid that is complementary to the coding strand or mRNA of a gene encoding a signaling pathway component. The nucleic acid can also be targeted to the translational start and stop sites. Preferably, the antisense oligonucleotide consists of about 8 to 30 nucleotides; however, useful antisense oligonucleotides can also contain at least 40, 60, 85, 120, or more consecutive nucleotides that are complementary to pathway component mRNA or DNA, and may be as long as the full-length pathway component mRNA or gene.

By "dsRNA" is meant a ribonucleic acid molecule comprised of both a sense and an anti-sense strand. dsRNAs are typically used to mediate RNA interference. "RNA interference (RNAi)" describes the use of double-stranded RNA (dsRNA) to block gene expression. (See, for example, Fire et al., *Nature* 391:806-811, 1998.) As used herein, RNAi refers to the ATP-dependent targeted cleavage and degradation of a specific mRNA molecule through the introduction of small interfering RNAs or dsRNAs into a cell or an organism.

By "homologous" or "homolog" is meant any gene or protein sequence that bears at least 30% homology, more preferably 50%, 75%, 85%, 90%, 95%, or 99% homology to a known gene or protein sequence over the length of the comparison sequence. A "homologous" protein may also have at least one biological activity of the comparison protein. For polypeptides, the length of comparison sequences will generally be at least 20 amino acids, preferably at least 30 amino acids, more preferably at least 50 amino acids, and most preferably 75 amino acids or more. For nucleic acids, the length of comparison sequences will generally be at least 60 nucleotides, preferably at least 90 nucleotides, more preferably at least 150 nucleotides, and most preferably at least 225 nucleotides.

By "operably linked" is meant that a protein coding sequence and a regulatory sequence(s) are connected in such a way as to permit expression of the protein coding sequence when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in *Remington's Pharmaceutical Sciences*, (20$^{th}$ edition), ed. A. Gennaro, 2000, Lippincott, Williams & Wilkins, Philadelphia, Pa.

By "small interfering RNA (siRNA)" is meant an isolated dsRNA molecule, at least 10 nucleotides in length and preferably not greater than 50 nucleotides in length. Preferably, siRNAs are 19-25 nucleotides in length. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23-nucleotide RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNAi.

By "specifically binds" or "specific binding" is meant an interaction between a ligand molecule and a substrate molecule where the interaction is characterized as having high affinity (<$10^{-6}$ M) and high specificity (does not substantially recognize other molecules obtained from the same biological sample). For example, the interaction between an antibody and the protein or epitope against which it was raised, is considered specific binding. Additionally, the interaction between sense and antisense polynucleotides, wherein the binding can occur under high stringency conditions, is another example of specific binding.

By "substantially identical" is meant a polypeptide or nucleic acid exhibiting at least 75%, but preferably 85%, more preferably 90%, most preferably 95%, or even 99% identity to a reference amino acid or nucleic acid sequence. For polypeptides, the length of comparison sequences will generally be at least 20 amino acids, preferably at least 30 amino acids, more preferably at least 40 amino acids, and most preferably 50 amino acids. For nucleic acids, the length of comparison sequences will generally be at least 60 nucleotides, preferably at least 90 nucleotides, and more preferably at least 120 nucleotides. Most preferably, polypeptide sequences differ only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

BRIEF DESCRIPTION OF THE DRAWINGS

FIG. 1 is a table showing representative examples of TGF-β family members, further subdivided into subfamilies.

DETAILED DESCRIPTION

Figure 2:
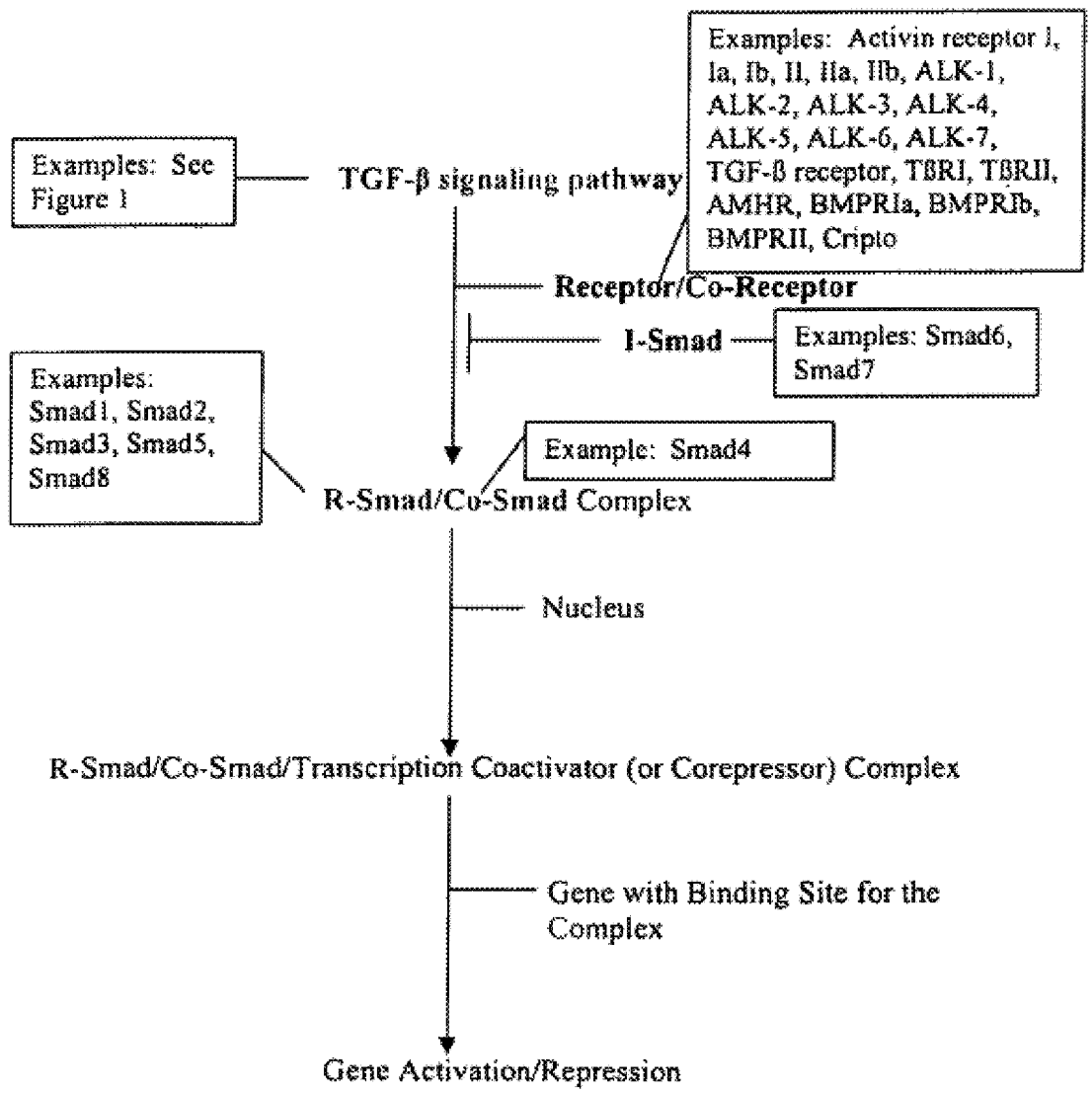
FIG. 2 is a schematic diagram illustrating the basic architecture of the signal transduction pathway of a TGF-β family member (TGF-β signaling pathway), and sets forth examples of the various signaling pathway components involved. Briefly, signaling is initiated by binding of a TGF-β family member to its respective receptor. The receptor generally is a serine-threonine kinase receptor complex consisting of two distinct transmembrane proteins, the type I and type II receptors. Ligand binding to the receptor induces the type I and type II receptors to associate, and causes the type II receptor to phosphorylate (and thus activate) the type I receptor, which, in turn, phosphorylates particular members of the R-Smad family of intracellular mediators. Phosphorylation induces the accumulation of R-Smads in the nucleus as heteromeric complexes with a Co-Smad. These complexes specifically associate with various transcriptional coactivators or corepressors in the nucleus, thereby differentially regulating gene expression via transcription, and converting a TGF-β signaling pathway signal to a distinct biological phenotype. Inhibitory Smads (I-Smads) interfere with TGF-β signaling through interactions with receptor or activated R-Smad.

The invention provides methods for treating neurodegenerative diseases (e.g., Parkinson's Disease or Alzheimer's Disease) in a patient by generating dopaminergic neurons, particularly A9 or A10 dopaminergic neurons, and transplanting these dopaminergic neurons into the brain of the patient. The dopaminergic neurons are generated from pluripotent cells by inhibiting a pathway component of a TGF-β signaling pathway and overexpressing one or more cell fate-inducing polypeptides in the pluripotent cells.

The pluripotent cells used in the methods of the invention may be mouse, rat, porcine, non-human primate, or human pluripotent cells. Pluripotent cells useful in the methods of this invention are stem cells into which with one or more cell fate-inducing genes (e.g., Nurr-1, PTX3, Phox 2a, AP2, and Shh) have been inserted and in which a pathway component of a TGF-β signaling pathway has been inhibited. Methods for isolating, culturing, and genetically modifying pluripotent cells are well known in the art. Although embryonic stem cells are referred to throughout the specification, any pluripotent cell may be substituted for the embryonic stem cells.

Normally, transplanted embryonic stem cells differentiate into cells of neuroectodermal, endodermal, and mesodermal lineage. Although differentiation along a neuroectodermal lineage is favored in untreated stem cells transplanted into the nervous system, this type of undirected differentiation results in the production of some cells that would not be useful for replacing the DA neurons that are lost in PD. Consequently, methods that promote differentiation of embryonic stem cells in vitro into neuroectodermal cell types, and transplantation of the DA neurons thus generated into the brain of a patient suffering from a neurodegenerative disease can prove more efficient than other transplantation methods in treating neurodegenerative diseases, such as PD.

We have discovered that the inhibition of particular TFG-β signaling pathways in combination with the overexpression of one or more cell fate-inducing polypeptides promotes the differentiation of embryonic stem cells into cells of neuroectodermal origin. Further, these neuroectodermal cells adopt a dopaminergic phenotype and are, therefore, suitable for replacing the dopaminergic cells that degenerate in patients having certain neurodegenerative diseases, such as PD.

Identification of Subtypes of Dopaminergic Neurons

Certain proteins, preferentially expressed in A10 cells, may play a critical role in resistance to neurodegenerative processes in PD, whereas proteins preferentially expressed in A9 cells may be responsible for their susceptibility to degeneration in PD. Indeed, studies have reported several proteins that are differentially expressed in A9 and A10 (Table 1). Differences in expression patterns are used to distinguish cultured A9-type DA neurons from other DA neurons for subsequent manipulation and transplantation.

TABLE 1

Differential Expression in A9 Compared to A10 DA Neurons

|     | Protein | Species | Method of Detection |
| --- | --- | --- | --- |
| A9 | DAT | Primate Human | In situ hybridization |
|  | $D_2$ receptor | Human Primate | In situ hybridization |
|  | Neuromelanin | Human |  |
|  | GIRK-2 | Mouse Rat | Immunohistochemistry, In situ hybridization |
|  | AHD-2 | Rat | Immunohistochemistry |
|  | EphB1 receptor Ephrin B2 ligand | Mouse | In situ hybridization |
|  | mGluR1α | Primate | Immunohistochemistry |
| A10 | Calbindin $D_{28}K$ | Rodent Primate Human | Immunohistochemistry, In situ hybridization |
| | Estrogen-β Receptor | Mouse | Immunohistochemistry |
| | Neurotrophin-3 (NT-3)/trkC | Human Rodent | Immunohistochemistry |
| | BDNF/trkB | Human Rodent | Immunohistochemistry |

Some differentially expressed proteins include, for example, calbindin D28K, an intracellular calcium binding protein, that has been used to distinguish resistant from vulnerable DA neurons in PD patient brain and animal models of PD, because it is colocalized in the resistant DA population (mostly A10). Another of these proteins is G-protein-gated inwardly rectifying potassium channel (GIRK) which generates a slow inhibitory postsynaptic potential (IPSP) via activation of D2 or GABA-B receptors and controls the membrane excitability of DA neurons. GIRK channels modulate the release of DA from synaptic terminal of DA cells to striatum. Among four isoforms of GIRK, only GIRK2 is exclusively expressed in the SNc and lateral ventral tegmental area (VTA). A potential role of GIRK2 in specific A9 DA neuron pathology has been found in weaver mice, which have a spontaneous mutation in the GIRK2 gene and display PD-like patterns of DA cell degeneration. The absence of the GIRK2 mutation in PD, however, has made it difficult to find a correlation to PD pathology.

Differentiation of ES Cells into Dopaminergic Neurons

Cell Fate-inducing Genes

Recently, progress has been made toward our understanding of the transcriptional control mechanisms for neuronal differentiation and specification of neurotransmitter identity. In DA neurons, a new orphan member of the nuclear receptor superfamily, Nurr1, was isolated and found to be co-expressed with TH in CNS DA neurons such as substantia nigra and olfactory bulb. Knock-out mice studies have demonstrated that Nurr1 is essential for the later stages of DA cell development by inducing a DA phenotype (Zetterstrom et al. *Science* 276: 248-250, 1997; Castillo et al. *Mol. Cell. Neurosci.* 11: 36-46, 1998; Saucedo-Cardenas et al *Proc. Natl. Acad. Sci. USA* 95: 4013-4018, 1998). In Nurr1-null mice, precursor neurons of the midbrain area formed but did not acquire the DA phenotype, either in the SNc (A9) or the VTA (A10); strongly suggesting that Nurr1 regulates DA neuron development by inducing the DA phenotype. Furthermore, the TH gene is a direct target of Nurr1 (Kim et al. *J. Neurochem.* 85: 622-634, 2003).

Wagner et al. (*Nat. Biotechnol.* 17: 653-659, 1999) has demonstrated that overexpression of Nurr1, along with additional factors, was able to induce neural stem cells to TH+ phenotype. In this study, the C17.2 cell line, an immortalized multipotent cell line derived from developing mouse cerebellum, was stably transfected with Nurr1. Most Nurr1-overexpressing clones adopted a neuronal fate after low density passage to serum free medium. At this stage, however, no TH expression was detected in any of Nurr1-expressing clones. Interestingly, co-culture with E16 rat VM cells induced a TH+ phenotype in two of the Nurr1-expressing clones. When combined with additional factors such as the synthetic retinoid analog (SR11237), bFGF, and EGF, more than 80% of cells were induced to express TH. Exogenous expression of Nurr1 in mES cells also results in an enhanced differentiation to the DA fate with a high efficiency (62 and 78% of TH+/Tuj1+ neurons, respectively) (Chung et al. *Eur. J. Neurosci.* 16: 1829-1838, 2002; Kim et al., *Nature* 418: 50-56, 2002).

Another candidate transcription factor for midbrain DA neuron fate is the homeobox protein Pitx3 (or its rat homologue, Ptx3) because of its highly restricted expression in the midbrain DA neurons in the brain and the developing lens. Recent studies have demonstrated that subsets of DA neurons in the SNc and the nigrostriatal pathway fail to develop properly in Pitx3-deficient aphakia mice and that these deficits are evident in newborn mice. Dopamine levels are severely reduced (by about 90%) in the dorsal striatum (see, for example, Hwang et al. *Brain Res. Mol. Brain. Res.* 114: 123-131, 2003). Notably, A10 DA neurons are largely spared in the aphakia mice, suggesting that Pitx3 may regulate the specification and survival of the A9 subset of DA neurons.

These gain-of-function studies in ES cells indicate that Nurr1 and Pitx3 may play co-operative but distinct roles for specific DA neuron development and it is optimal to express both Nurr1 and Pitx3 in ES cells to efficiently generate A9-like DA neurons for transplantation.

TGF-β Superfamily Members

Differentiation of ES cells overexpressing a cell fate-inducing gene into dopaminergic neurons can be facilitated by blocking competing pathways, e.g., pathways that lead to differentiation into cell types of mesodermal or endodermal origin. Examples of these competing pathways include, but are not limited to, signaling pathways for TGF-β superfamily members Nodal, Activin, BMP2, BMP4, and BMP7, which have been shown to be important for endoderm and mesoderm differentiation. Signaling pathways for these TGF-β superfamily members involve various receptors, SMAD proteins, and other regulator proteins, including, for example, BMPRIa, BMPRIb, BMPRII, activin receptor I, activin receptor II, activin receptor IIb, TGF-β receptor, ALK1, ALK2, ALK3, ALK4, ALK6, ALK7, Smad2, Smad3, Smad4, Smad5, Smad6, Cryptic, and Cripto. Accordingly, by inhibiting any one of these TGF-β family members, signaling pathway components thereof, or other signaling pathway components that lead to endoderm or mesoderm differentiation, including Nodal, Activin, BMP2, BMP4, and BMP7, differentiation into a cell of neuroectodermal origin (e.g., DA neuron) is favored.

In addition to inhibiting a TGF-β signaling pathway component, cell fate-inducing polypeptides such as Nurr-1 and or PTX3 are overexpressed to improve the yield of DA neurons from differentiating ES cells in vitro. It will be apparent to one of skill in the art that the timing and extent of inhibition of the pathway component and overexpression of one or more cell fate-inducing polypeptides will vary depending on the methods and dosages used. For example, inhibition by gene knockout technology persists throughout the lifetime of an ES cell, whereas inhibition via antisense oligonucleotides is generally transient such that antisense oligonucleotides need to be reapplied. In the latter case, one of skill in the art would be able to readily determine when and how much of the antisense oligonucleotide to reapply to promote DA neuron differentiation.

The method of differentiating ES cells into DA neurons in vitro has been reported (Lee et al., *Nat. Biotechnol.* 18:675-679, 2000). By way of example, this procedure is modified to accommodate inhibition of a pathway component and overexpression of one or more cell fate-inducing polypeptides to obtain more DA neurons. Briefly, D3 (A.T.C.C.; Rockland, Md.) and B5 (Hadjantonakis et al., *Mech. Dev.* 76:79-90, 1998) ES cells are differentiated into embryoid bodies (EBs) in suspension culture for four days after removal of leukemia inhibitory factor (LIF). If inhibition of a pathway component is through gene knockout technology, recombinant ES cell lines with structurally disrupted endogenous pathway component genes are the appropriate starting material. Otherwise, inhibitory treatments described in this specification (e.g., overexpressing antisense oligonucleotides, small interfering RNA, inhibitory antibodies, or dominant negative protein variants) that have a transient effect are performed prior to differentiation into embryoid bodies, and/or at other points in the procedure that a person of skill in the art deems appropriate. Similarly, treatments to overproduce one or more cell fate-inducing polypeptides that have a transient effect are performed prior to differentiation into embryoid bodies, and/or at other points in the procedure that a person of skill in the art deems appropriate. The EBs are then plated onto adhesive tissue culture surface in the ES cell differentiation medium. After 24 hr of culture, nestin-positive cells are selected by replacing the medium by serum-free ITSFn medium (Rizzino et al., *Proc. Natl. Acad. Sci. USA* 77:457-461, 1980; Okabe et al., *Mech. Dev.* 59:89-102, 1996). After 6-10 days of selection, nestin-positive cells are expanded by dissociating the cells by trypsinization and subsequent plating on tissue culture plastic containing N2 medium (Johe et al., *Genes Dev.* 10:3129-3140, 1996) supplemented with laminin (1 mg/ml) and bFGF (10 ng/ml). After expansion for six days, the medium is changed every two days. Differentiation is induced by removal of bFGF from the medium. Signaling molecules known to induce the $TH^+$ phenotype, e.g., analog of cAMP, retinoic acid, Shh, FGF8, and ascorbic acid (Kalir et al., *J. Neurochem.* 57:458-464, 1991; Kim et al., *Proc. Natl. Acad. Sci. USA* 90:3471-3475, 1993; Lee et al., *Nat. Biotechnol.* 18:675-679, 2000) are used and compared in naive and transgenic ES cell lines. Marker expression is examined by immunocytochemistry and RT-PCR analysis. To determine the molecular changes between nestin-positive neural progenitor cells and more differentiated TH+ neurons, EBs are collected from each stage of in vitro differentiation as described above. Poly (A)+ RNA are isolated and the probes prepared subsequently.

A strategy to isolate selectively homogenous populations of DA neurons has been developed. See U.S. Ser. No. 09/626, 677. A recent study showed that neuroepithelial cells can be efficiently selected from differentiated ES cells by inserting a selectable marker gene into the Sox2 gene that is specifically expressed in neuroepithelial cells (Li et al., *Curr. Biol.* 8:971-974, 1998). For DA neurons, dopamine transporter (DAT) is another specific marker protein in addition to that of TH. Introduction of a selectable marker/reporter gene cassette into the DAT or TH gene of ES cells allows the selective isolation of a homogenous cell population of DA neurons.

Methods for Regulating the Signaling Pathway of a TGF-β Signaling Pathway in Embryonic Stem Cells in Vitro Prior to Transplantation Inhibition of a pathway component in embryonic stem cells in vitro can be accomplished using a variety of tools, including, but not limited to, gene knockout of the nucleic acid encoding the signaling pathway component; antisense oligonucleotide and small interfering RNA directed and specific to the mRNA encoding the signaling pathway component; antibodies specific to the pathway component and whose binding with the pathway component leads to inactivation of the signaling pathway component; and dominant negative versions of the signaling pathway component. Thus, the invention concerns the use of nucleic acids (e.g., DNA for gene knockout; DNA encoding antisense RNA; DNA encoding siRNA; DNA encoding dominant negative variant of signaling pathway component; antisense oligonucleotides; antisense RNA; siRNA) and proteins (e.g, antibodies specific to a signaling pathway component; dominant negative variant of a signaling pathway component) in inhibiting a pathway component of a TGF-β family member. These methods are discussed, as well as modes of introducing the inhibiting molecule into the ES cell.

Gene Knockout

The present invention features the use of gene knockout technology to structurally disrupt the endogenous nucleic acid encoding a pathway component of a TGF-β superfamily member. Methods for disruption of specific genes in the genome are well-known in the art (see, e.g., Bronson et al., *J. Biol. Chem.* 269:27155-27158, 1994; Bunz, *Curr. Opin. Oncol.* 14:73-78, 2002). Examples of genetic alterations that may be produced by these methods include disruptive deletion, conditional alleles that allow for tissue-specific or temporal control of gene expression, point mutations, and targeted insertions of any nucleic acid of interest (Abuin et al., *Trends Biotechnol.* 20:36-42, 2002). The disrupting DNA may be introduced into the ES cell using methods known in the art. Cells determined to have had the inactivating DNA stably integrated into the genome at the desired locus (e.g., by using negative or positive selection with selectable markers, and analyzing genomic structure) may be used for transplantation.

In the present invention, the disrupting DNA (e.g., DNA highly homologous to the endogenous target DNA that encodes a pathway component but with a disruption early on of the open reading frame encoding the signaling pathway component) replaces the endogenous DNA in the genome encoding the signaling pathway component, resulting in a decrease in production of functional signaling pathway component. Methods for assaying levels of protein expression are also well known in the art and include Western blotting, immunoprecipitation, and ELISA.

Antisense

The present invention features the use of antisense oligonucleotides to inhibit translation of a signaling pathway component. By binding to the complementary nucleic acid sequence (the sense or coding strand), antisense oligonucleotides are able to inhibit protein expression through the enzymatic cleavage of the RNA strand by RNAse H. Methods for selecting and preparing antisense oligonucleotides are well known in the art. For an example of the use of antisense oligonucleotides to downregulate expression of a protein, see U.S. Pat. No. 6,410,322, incorporated herein by reference. Ribozyme technology may also be used to incorporate ribozyme catalytic centers into antisense RNAs, creating the ability to site-specifically cleave target RNA substrates (Rossi, *Trends Biotechnol.* 13:301-306, 1995). Methods for assaying levels of protein expression are also well known in the art and include western blotting, immunoprecipitation, and ELISA.

In the present invention, the nucleic acids may include any modification that enhances the stability or function of the nucleic acid in any way. Examples include modifications to the phosphate backbone, the internucleotide linkage, or to the sugar moiety.

In some embodiments, the nucleic acid is operably linked to a suitable promoter (e.g., the human cytomegalovirus, simian virus 40, or metallothionein promoters), and regulated by any desired mammalian regulatory element. The Rous sarcoma virus (RSV) (Davis et al., *Hum. Gene Ther.* 4:151-159, 1993) and mouse mammary tumor virus (MMTV) promoters may also be used. The promoter must be capable of driving expression of the encoding nucleic acid in the desired target host cell. The selection of appropriate promoters can readily be accomplished. In one preferred embodiment, one would use a high expression promoter. Certain proteins can be expressed using their native promoter. Other elements that can enhance expression can also be included (e.g., enhancers or a system that results in high levels of expression such as a tat gene and tar element). For example, if desired, enhancers known to direct preferential gene expression in neuron cells may be used to direct expression. The recombinant vector can be a plasmid vector such as pUC118, pBR322, or other known plasmid vectors, that includes, for example, an *E. coli* origin of replication (see, Sambrook, et al., Molecular Cloning: A Laboratory Manual, Cold Spring Harbor Laboratory press, 1989). The plasmid vector may also include a selectable marker such as the β-lactamase gene for ampicillin resistance, provided that the marker polypeptide does not adversely affect the metabolism of the organism being treated. The nucleic acid can also be attached to a binding moiety in a synthetic delivery system, such as the system disclosed in WO 95/22618.

The nucleic acid can be introduced into the cells by any means appropriate for the vector employed. Many such methods are well known in the art (Sambrook et al., supra, and Watson et al., Recombinant DNA, Chapter 12, 2d edition, Scientific American Books, 1992). Recombinant vectors can be transferred by methods such as calcium phosphate precipitation, electroporation, liposome-mediated transfection, gene gun, microinjection, viral capsid-mediated transfer, polybrene-mediated transfer, protoplast fusion, etc. For a review of the procedures for liposome preparation, targeting and delivery of contents, see Mannino et al. (*Bio Techniques* 6:682-690, 1988), Felgner et al. (*Bethesda Res. Lab. Focus* 11:21, 1989), and Maurer (*Bethesda Res. Lab. Focus* 11:25, 1989). Non-limiting examples of a commercial preparation that can be used for transfection are Lipofectamin PLUS (GIBCO BRL, Lifetechnologies, Gaithesburg, Md., USA), TransIT-TKO3 (Mirus, Cat. # MIR 2150), Transmessenger3 (Qiagen, Cat. #301525), and Oligofectamine-3 (Invitrogen, Cat. # MIR 12252-011). Protocols for each transfection reagent are available from the manufacturer.

RNA Interference

The present invention also features the use of RNA interference (RNAi) to inhibit expression of a signaling pathway component. RNA interference (RNAi) is a recently discovered mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene.

The specific requirements and modifications of dsRNA are described in PCT application number WO01/75164 (incorporated herein by reference). While dsRNA molecules can vary in length, it is most preferable to use siRNA molecules which are 21-to 23-nucleotide dsRNAs with characteristic 2-to 3-nucleotide 3' overhanging ends typically either (2'-deoxy)thymidine or uracil. The siRNAs typically comprise a 3' hydroxyl group. Single stranded siRNA as well as blunt ended forms of dsRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

Alternatively siRNA can be prepared using any of the methods set forth in PCT number WO01/75164 (incorporated herein by reference) or using standard procedures for in vitro transcription of RNA and dsRNA annealing procedures as described by Elbashir et al. (*Genes & Dev.* 15:188-200, 2001). siRNAs are also obtained as described by Elbashir et al. by incubation of dsRNA that corresponds to a sequence of the target gene in a cell-free *Drosophila* lysate from syncytial blastoderm *Drosophila* embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs, and the RNAs can then be eluted from the gel slices. In addition, chromatography (e.g., size exclusion chromatography), glycerol gradient centrifugation, and affinity purification with antibody can be used to isolate the 21 to 23 nt RNAs.

In the present invention, the dsRNA, or siRNA, is complementary to the nucleotide sequence of an mRNA encoding a pathway component and can reduce or inhibit expression of the signaling pathway component. Preferably the decrease in expression of the pathway component is at least 10% relative to cells treated with a control dsRNA or siRNA, more preferably 25%, and most preferably at least 50%. Methods for assaying levels of protein expression are also well known in the art and include western blotting, immunoprecipitation, and ELISA.

Antibodies

The use of compounds, such as antibodies, to specifically bind to a pathway component and block endoderm or mesoderm differentiation pathways may help promote differentiation of ES cells into DA neurons. This would help improve current treatments of neurodegenerative diseases or disorders like PD.

The present invention features antibodies that bind specifically to a pathway component of a TGF-β superfamily member that is important for endoderm and mesoderm differentiation. The antibodies are used to inhibit the pathway component and the most effective mechanism is believed to be through direct blocking of the active site(s) of the signaling pathway component; however, other mechanisms cannot be ruled out. Methods for the preparation and use of antibodies for therapeutic purposes are described in several patents including U.S. Pat. Nos. 6,054,297; 5,821,337; 6,365,157; and 6,165,464 and are hereby incorporated by reference. Antibodies can be polyclonal or monoclonal; however, monoclonal antibodies are normally preferred.

Monoclonal antibodies, particularly those derived from rodents including mice, have been used for the treatment of various diseases; however, there are limitations to their use including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood* 62:988-995, 1983; Schroff et al., *Cancer Res.* 45:879-885, 1985). The art has attempted to overcome this problem by constructing "chime c" antibodies in which an animal antigen-binding variable domain is coupled to a human constant domain (U.S. Pat. No. 4,816,567; Morrison et al., *Proc. Natl. Acad. Sci. USA* 81:6851-6855, 1984; Boulianne et al., *Nature* 312:643-646, 1984; Neuberger et al., *Nature* 314:268-270, 1985).

In the present invention, the antibodies specifically bind a pathway component and inhibit functional activity of the signaling pathway component. Preferably the decrease in activity of the pathway component is at least 10% relative to cells treated with a control antibody, more preferably 25%, and most preferably at least 50%. Methods for assaying activity levels of various signaling pathway components of TGF-β superfamily members are known in the art. For example, activity level of the pathway component may be indicated by the transcription level of the genes that are regulated by the TGF-β superfamily member.

Dominant Negatives

Dominant negative constructs (i.e., constructs encoding a dominant negative gene product of a signaling pathway component) are generated according to methods known in the art. These constructs are then introduced into ES cells using methods known in the art, including calcium phosphate precipitation, electroporation, liposome-mediated transfection, gene gun, microinjection, viral capsid-mediated transfer, polybrene-mediated transfer, protoplast fusion, etc. Typically, a dominant negative gene encodes a mutant pathway component which, when overexpressed, disrupts the activity of the wild type signaling pathway component. Transfected cells having an increased likelihood to differentiate into DA neurons because of the inhibition of endoderm and mesoderm differentiation pathways by dominant negative polypeptide-mediated inhibition of a signaling pathway component, are useful in the invention.

In the present invention, the dominant negative polypeptide inhibits functional activity of the signaling pathway component. Preferably the decrease in activity of the pathway component is at least 10% relative to cells treated with a control polypeptide, more preferably 25%, and most preferably at least 50%. Methods for assaying activity levels of various signaling pathway components of TGF-β superfamily members are known in the art. For example, activity level of the pathway component may be indicated by the transcription level of the genes that are regulated by the TGF-β superfamily member.

Dominant negative constructs have been utilized previously to interfere with no mal polypeptide function (Lagna et al., *Curr. Top. Dev. Biol.* 36:75-98, 1998). For example, Hemmati-Brivanlou et al. (*Cell* 77:273-281, 1994) inhibited activin receptor signaling by expressing a dominant negative activin receptor, and showed that inhibition of activin receptor signaling promotes neuralization. Dominant interfering Derriere proteins have also been used to explore function of wild-type derriere, a TGF-β signaling pathway (Sun et al., *Development* 126: 1467-1482, 1999).

Methods for Overexpressing One or More Cell Fate-Inducing Polypeptides in Pluripotent Cells In Vitro Prior to Transplantation One or more cell fate-inducing polypeptides may be overexpressed in embryonic stem cells using any of the standard methods known in the art (see, for example, Wagner et al. *Nat. Biotechnol.* 17: 653-659, 1999; Chung et al. *Eur. J. Neurosci.* 16: 1829-1839, 2002; Kim et al. *Nature* 418: 50-56, 2002;

U.S. patent application Ser. Nos. 09/626,677, filed Jul. 27, 2000, and 09/917,126, filed Jul. 27, 2001; hereby incorporated by reference). A common procedure employed makes use of exogenous DNA. In the present invention, constructs containing a polynucleotide encoding a cell fate-inducing polypeptide that is operably linked to a promoter are generated and then introduced into embryonic stem cells. Above normal levels of the cell fate-inducing polypeptide are produced by the transfected embryonic stem cells, owing to the extra amount of the cell fate-inducing polypeptide produced off the construct. Methods of generating such constructs and introducing them into cells are known in the art.

By way of example, construction of a Nurr-1 expressing ES cell line is described. Nurr-1 cDNA was subcloned into the SacI site in pIRES2-EGFP (Clontech). Nurr-1-containing plasmids were amplified in E. coli and purified with the QIAGEN plasmid purification kit (QIAGEN Inc.). The constructs functionality was tested by demonstrating its ability to induce tyrosine hydroxylase (TH) reporter gene expression in cell lines such as BE(2)C cells, followed by β-galactosidase and CAT-assays. pIRES2-EGFP with and without Nurr-1 insert was linearized with Afl II and isolated after 1% agarose gel electrophoresis for transfection to embryonic stem (ES) cells.

ES D3 cells were seeded into gelatin coated dishes to an approximate confluence of 25%. The following morning, the cells were transfected using Lipofectamin PLUS (GIBCO BRL, Life technologies, Gaithersburg, Md., USA) according to the manufacturer's protocol. Briefly, 30 µg DNA in 750 µl serum free media and 60 µl PLUS were mixed and incubated at RT for 15 minutes after which 60 µl Lipofectamin in 750 µl serum free media was added and the mixture incubated for another 15 minutes at RT. The mixture was added drop-wise to cultured cells in a 100 mm dish containing 5 ml ES-media (450 ml high glucose DMEM, 50 ml horse serum (HS), 5 ml 100×L-glutamine, 5 ml Hees, 5 ml 100×NEAR, 5 ml β-mercaptoethanol and 100 l. LIF 30 µg/ml).

After 24 h, 5 ml fresh ES-media was added and after another 6 h, cells were split and cultured in ES media containing 500 µg/ml neomycin (G418 Sulfate, Clontech, Palo Alto, Calif., USA) for selection. Leftover cells were frozen in ES-freezing media (90% horse serum and 10% DMSO). The concentration of neomycin needed for selection was determined by culturing untransfected and transfected cells in a range of titers of neomycin.

Cells split 30 h after transfection were pooled together, cell stocks were made, and cells were cultured to be used for RT-PCT analysis and immunocytochemistry. Fresh transfected cells (frozen 30 h after transfection) were thawed and seeded, highly diluted, in gelatin coated dishes and grown for five days in ES-media with G418 (500 µg/ml). Well-isolated colonies were picked using cloning cylinders and cloning discs and transferred to a gelatin coated 24 well plate. Cells were grown to confluency (between 10 and 14 days), harvested and frozen in 0.5 ml ES-freezing media. A small number of the cells (~⅛) were expanded for RNA preparation. Clones were screened to detect Nurr-1-expression, using GeneAmp Thermostable rTth Reverse Transcriptase RNA PCT Kit (PERKIN ELMER, Branchburg, N.J., USA) according to the manufacturer's protocol. These non-human primate ES cell lines provided an accurate in vitro model for human transplantation studies.

Multiple Nurr-1-expressing ES cell lines isolated after neomycin selection were used for in vivo transplantation as well as in vitro differentiation into the DA phenotype. To further direct the differentiation process of Nurr-1-expressing ES cells into the DA phenotype in vitro, a pathway component (e.g., Nodal or Cripto) of a TGF-β signaling pathway can be inhibited according to the invention. These Nurr-1-expressing ES cells in which a pathway component of a TGF-β signaling pathway has been inhibited can thus serve as a source of DA neurons. Protocols employed here are well-known by those skilled in the art and may be found, for example, in Ausubel et al., *Current Protocols in Molecular Biology*, John Wiley & Sons, New York, N.Y., 1997.

Embryonic Stem Cell Culture

A mouse blastocyst-derived ES cell line D3 (wild type) was obtained from the American Type Culture Collection (Accession Number CRL-1934). Undifferentiated ES cells were maintained on gelatin-coated dishes in DMEM (GIBCO/BRL) supplemented with 2 mM glutamine (GIBCO/BRL), 0.001% β-mercaptoethanol, 1× nonessential amino acids (GIBCO/BRL), 10% donor horse serum (HyClone), and human recombinant leukemia inhibitory factor (2,000 units/ml, R & D Systems). Early passage cultures were frozen in 90% horse serum/10% DMSO, and aliquots of cell vials were stored in liquid nitrogen. ES cells were thawed for use and cultured for 2 weeks in the presence of leukemia inhibitory factor. The cells were then trypsinized (0.05% trypsin-EDTA, GIBCO), resuspended, and seeded at $5 \times 10^6$ cells in 15 ml of DMEM in a 100-mm Fisher brand bacteriological grade Petri dish in the absence of leukemia inhibitory factor. Horse serum was replaced in the culture medium by 10% fetal calf serum (FCS) (HyClone). ES cells did not adhere to the dish but instead formed small aggregates (embryoid body). The ES cells were incubated for 4 days at 37° C. before the cells were transferred to a 15-ml sterile culture tube and allowed to settle, centrifuged at 1,000 rpm for 5 min, collected, and rinsed once in $Ca^{2+}$ and $Mg^{2+}$-free Dulbecco's PBS (GIBCO/BRL). After rinsing, Dulbecco's PBS was removed, 1.5 ml of trypsin solution was added, and the cells were incubated for 5 min at 37° C. and then triturated with fire-polished Pasteur pipettes with decreasing aperture size to fully dissociate the cells. Finally, ES cells were spun at 1,000 rpm for 5 min, the trypsin solution was replaced with 200 µl of culture medium, and the viability and concentration of the ES cells were determined by using a hemocytometer after staining with acridine orange and ethidium bromide.

Embryonic stem cell lines can also be derived from human blastocysts using the following procedure. Fresh or frozen cleavage stage human embryos, produced by in vitro fertilization (IVF) are cultured to the blastocyte stage in G1.2 and G2.2 medium. These embryos are donated by individuals after informed consent and after institutional review board approval. Inner cell masses are isolated by immunosurgery, with a rabbit antiserum to BeWO cells, and plated on irradiated (35 grays gamma irradiation) mouse embryonic fibroblasts. Culture medium consists of 80% Dulbecco's modified Eagle's medium (no pyruvate, high glucose formulation; Gibco-BRL) supplemented with 20% fetal bovine serum (Hyclone), 1 mM glutamine, 0.1 mM β-mercaptoethanol (Sigma), and 1% nonessential amino acid stock (Gibco-BRL). After 9-15 days, the inner cell mass-derived outgrowths are dissociated into clumps either by exposure to $Ca^{2+}/Mg^{2+}$ free phosphate-buffered saline with 1 mM EDTA, by exposure to dispase, or by mechanical dissociation with a micropipette and replated on irradiated mouse embryonic fibroblasts in fresh medium. Individual colonies with a uniform undifferentiated morphology are individually selected by micropipette, mechanically dissociated into clumps, and replated. Once established and expanded, cultures are passaged by exposure to type IV collagenase (1 mg/ml; Gibco-BRL) or by selection of individual colonies by micropipette. Clump sizes of about 50-100 cells are optimal. The resulting cells have a high ratio of nucleus to cytoplasm, prominent nucleoli, and a colony morphology similar to that of rhesus monkey ES cells. Cell lines can be cryopreserved and thawed when required.

Cell Transplantation

Transplantation can be allogeneic (between genetically different members of the same species), autologous (transplantation of an organism's own cells or tissues), syngeneic (between genetically identical members of the same species (e.g., identical twins)), or xenogeneic (between members of different species). Ordinarily, the DA neurons would be transplanted into the substantia nigra, the ventral tegmental area (VTA), the caudate, the putamen, the nucleus accumbens, the subthalamic nucleus, or any combination thereof, of the brain to replace the DA neurons whose degeneration resulted in PD. Transplantation into the substantia nigra, the caudate, or the putamen is performed because, although the cell bodies of A9 DA neurons are located in the substantia nigra, their axons extend into the forebrain structures where dopamine release occurs. In disease conditions where it is desirable to replace A10 DA neurons, the DA neurons (obtained from in vitro differentiation of ES cells) are transplanted into the VTA, the nucleus accumbens, or both regions of the brain. In the late stages of PD, cognitive and behavioral disturbance may be generated from DA loss and synaptic dysfunction in the caudate, cerebral cortex deep layers, nucleus accumbens, and substantia nigra regions of the brain. Thus, the ventral tegmental DA neuronal phenotype of A10 would be specifically transplanted to these regions to replace lost A10 DA functions. In particular, transplantation of A10 DA neurons, or cells primed to differentiate into A10 DA neurons, to the caudate nucleus would be the preferred and most effective replacement.

Transplantation of the cells of the invention into the brain of the patient with a neurodegenerative disease results in replacement of lost, non-, or dysfunctional DA neurons. The cells are introduced into a subject with a neurodegenerative disease in an amount suitable to replace the dysfunctional DA neurons such that there is an at least partial reduction or alleviation of at least one adverse effect or symptom of the disease. The cells can be administered to a subject by any appropriate route that results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months. One transplantation method that can be used to deliver the cells to a subject is described by Bjorklund et al. (*Proc. Nat. Acad. Sci. USA* 99:2344-2349, 2002). The DA neurons can be administered in a physiologically compatible carrier, such as a buffered saline solution. To treat disorders characterized by neuron degeneration in a human subject, a population of DA neurons as a suspension of 25,000 to 250,000 cells per microliter in a pharmaceutically acceptable carrier, such that the cells form, in the patient, a population of cells in which at least 5%, 10%, 20%, 30%, 40%, 50%, 60%, 70%, 80%, or 90% of the cells are dopaminergic, is introduced into the patient. Preferably, the suspension is 50,000 to 200,000 cells per microliter. More preferably, the suspension is 75,000 to 150,000 cells per microliter.

To accomplish these methods of administration, the cells of the invention can be inserted into a delivery device that facilitates introduction by injection or implantation of the cells into the subject. Typically, the cells are injected into the target area as a cell suspension. Alternatively, the DA neurons can be embedded in a solid or semisolid support matrix when contained in such a delivery device.

The solution includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, or thimerosal. Solutions of the invention can be prepared by incorporating the cells as described herein in a pharmaceutically acceptable carrier or diluent and, as required, other ingredients.

Support matrices in which the DA neurons of the invention can be incorporated or embedded include matrices which are recipient-compatible and which degrade into products that are not harmful to the recipient. Natural and/or synthetic biodegradable matrices are examples of such matrices. Natural biodegradable matrices include, for example, collagen matrices. Synthetic biodegradable matrices include synthetic polymers such as polyanhydrides, polyorthoesters, and polylactic acid. These matrices provide support and protection for the cells in vivo.

Prior to introduction into a subject, the DA neurons can be modified to inhibit immunological rejection. For example, to inhibit rejection of transplanted cells and to achieve immunological non-responsiveness in a transplant recipient, the methods of the invention can include alteration of immunogenic antigens on the surface of the cells prior to introduction into the subject. This step of altering one or more immunogenic antigens on the cells can be performed alone or in combination with administering to the subject an agent that inhibits T cell activity in the subject. Alternatively, inhibition of rejection of the transplanted cells can be accomplished by administering to the subject an agent that inhibits T cell activity in the subject in the absence of prior alteration of an immunogenic antigen on the surface of the transplanted cells. An agent that inhibits T cell activity is defined as an agent which results in removal (e.g., sequestration) or destruction of T cells within a subject or inhibits T cell functions within the subject. T cells may still be present in the subject but are in a non-functional state, such that they are unable to proliferate or elicit or perform effector functions (e.g., cytokine production, cytotoxicity, etc.). The agent that inhibits T cell activity may also inhibit the activity or maturation of immature T cells (e.g., thymocytes). A preferred agent for use in inhibiting T cell activity in a recipient subject is an immunosuppressive drug that inhibits or interferes with normal immune function. A preferred immunosuppressive drug is cyclosporin A. Other immunosuppressive drugs that can be used include, for example, FK506 and RS-61443. Additional therapeutic agents that can be administered include steroids (e.g., glucocorticoids such as prednisolone, methyl prednisolone, and dexamethasone).

EXAMPLE 1

In Vitro Differentiation Neuronal Differentiation of Smad4$^{-/-}$ and Cripto$^{-/-}$ Embryonic Stem Cells Smad4 and Cripto are key TGF-β signaling pathway components that control multiple aspects of embryogenesis, including mesodermal and epidermal cell development. Both Smad4$^{-/-}$ and Cripto$^{-/-}$ mice die prior to embryonic day 7.5 with severe developmental defects in gastrulation and axial organization, respectively.

ES Cell Culture and In Vitro Differentiation.

Wild type (WT) E14K and Smad4$^{-/-}$ (C8-13A1) ES cells were kindly provided by Drs. C. Sirard and Tak W. Mak, University of Toronto, Toronto, Canada). Wild type TC 1 and the Cripto$^{-/-}$ (clones CHG51 and CHG79) were kindly provided by Dr. M. M. Shen, UMDNJ-Robert Wood Johnson Medical School, New Jersey, USA. The ES cells were propagated and in vitro differentiated as described previously (Lee et al. *Nat. Biotechnol.* 18: 675-679, 2000; Chung et al. *Eur. J. Neurosci.* 16: 1829-1838, 2002).

Immunocytochemistry

Cells were analyzed by immunofluorescence staining as previously described (Chung et al., 2002) and examined using an LSM510 Meta confocal microscope equipped with ultraviolet, argon and helium/neon lasers (Carl Zeiss, Thornwood, N.Y.). The following primary antibodies were used: rabbit anti-glial fibrillary acidic protein; GFAP (DAKO, Carinteria, Calif.; 1:500), mouse anti-β-III-tubulin (Covance, Richmond, Calif.; 1:500), rabbit anti-β-III-tubulin (Covance; 1:2000), sheep anti-tyrosine hydroxylase; TH (Pel-Freez, Rogers, A K; 1:300), rabbit anti-TH (Pel-Freez; 1:300), mouse anti-TH (Pel Freez; 1:300), mouse anti-Nestin (Developmental Studies Hybridoma Bank, Iowa City, Iowa; 1 µg/ml), mouse anti-SSEA1 (Dev. Studies Hybridoma Bank; 1 µg/ml), rabbit anti-cytokeratin (Dako; 1:400), mouse anti-myosin (MF20, Dev. Studies Hybridoma Bank; 1 µg/ml). The secondary antibodies utilized were Alexa Fluor 488, 594, and 660 conjugated donkey immunoglobulin (Molecular Probes, Eugene, Oreg.; 1:500).

RNA Preparation and Semi-quantitative RT-PCR

Total RNA from plated cells at different stages in the differentiation protocol was prepared using TriReagent (Sigma) followed by treatment with DNAse I (DNA-free, Ambion). For RT-PCR analysis, 3-5 mg RNA was transcribed into cDNA with the SuperScript™ Preamplification Kit (Life Technologies) and oligo (dT) primers. The cDNA was then diluted 1:3 and 2.5% per reaction were analyzed in a PCR assay using the following mouse-specific primers:

```
β-actin:
                                          (SEQ ID NO: 1)
5'-GGTGATGACCTGGCCGTCAGGCAGCTCGTA-3'

(SEQ ID NO: 2)
5'-AACCCCAAGGCCAACCGCGAGAAGATGACC-3'

Nurr1:
                                          (SEQ ID NO: 3)
5'-CATGGACCTCACCAACACTG-3'

(SEQ ID NO: 4)
5'-GAGACAGGTGTCTTCCTCTG-3'

Tyrosine Hydroxylase (TH):
                                          (SEQ ID NO: 5)
5'-TCCTGCACTCCCTGTCAGAG-3'

(SEQ ID NO: 6)
5'-CCAAGAGCAGCCCATCAAAGG-3'

GBX2:
                                          (SEQ ID NO: 7)
5'-GAGCATCACACAGGGTTCTG-3'

(SEQ ID NO: 8)
5'-CACCTTTAAATCGCGCTCCTC-3'

Brachyury:
                                          (SEQ ID NO: 9)
5'-ACAATTCATCTGCTTGTCTGTCC-3'

(SEQ ID NO: 10)
5'-CGGTTGTTACAAGTCTCAGCAC-3'

HNF-4:
                                          (SEQ ID NO: 11)
5'-GAGGTCCATGGTGTTTAAGGAC-3'

(SEQ ID NO: 12)
5'-CTGCAGCAGGTTGTCAATCTTGG-3'

GATA4:
                                          (SEQ ID NO: 13)
5'-AGATGCGCCCCATCAAGACAG-3'

(SEQ ID NO: 14)
5'-CCGGAACACCCATATCCTAAG-3'

Tuj1:
                                          (SEQ ID NO: 15)
5'-AACTATGTAGGGGACTCAGACCTGC-3'

(SEQ ID NO: 16)
5'-TCTCACACTCTTTCCGCACGAC-3'

Nodal:
                                          (SEQ ID NO: 17)
5'-GAGGTGACCAAGCCACTCTCC-3'

(SEQ ID NO: 18)
5'-AGGGTTAGGACACTCGCCCTC-3'

Cripto:
                                          (SEQ ID NO: 19)
5'-GCAACTGTGAACATGATGTTCG-3'

(SEQ ID NO: 20)
5'-TGAGGTCCTGGTCCATCACG-3'
```

The primer sequences for amplifying the following genes were previously published: Otx2, En-1, and Nestin (Lee et al., 2000), Smad4 (Oxburgh et al. *Mech. Dev.* 112:207-211, 2002).

PCR reactions were carried out with 1×IN Reaction Buffer (Epicentre Technologies, Madison, Wis.), 1.4 nM of each primer, and 2.5 units of Taq I DNA polymerase (Promega, Madison, Wis.). Samples were amplified in an Eppendorf Thermocycler (Brinkmann Instruments, Westbury, N.Y.) under the following conditions: denaturing step at 95° C., 40 seconds; annealing step at 60° C., 30 sec; amplification step at 72° C., 1 min for 25 to 35 cycles and a final amplification step at 72° C., 10 min. For semi-quantitative PCR, cDNA templates were normalized by amplifying actin-specific transcripts and levels of gene transcription were detected by adjusting PCR cycling and primer design in such a way that each primer set amplified its corresponding gene product at its detection threshold to avoid saturation effects. Twenty to forty percent of the PCR products were analyzed in 7% polyacrylamide gels. Gels were then stained with ethidium bromide and visualized under UV light and photographed on Polaroid 3000 black and white prints. Photographs were scanned with an Epson (Epson Perfection 1640SU) scanner.

For evaluation of levels of gene expression, signal intensities (optical densities, OD) were measured using the StatView software program (National Institutes of Health, USA), version 1.61. After subtracting background signals, values were calculated as percent of the corresponding actin signals and plotted as relative unit OD.

Figure 3:
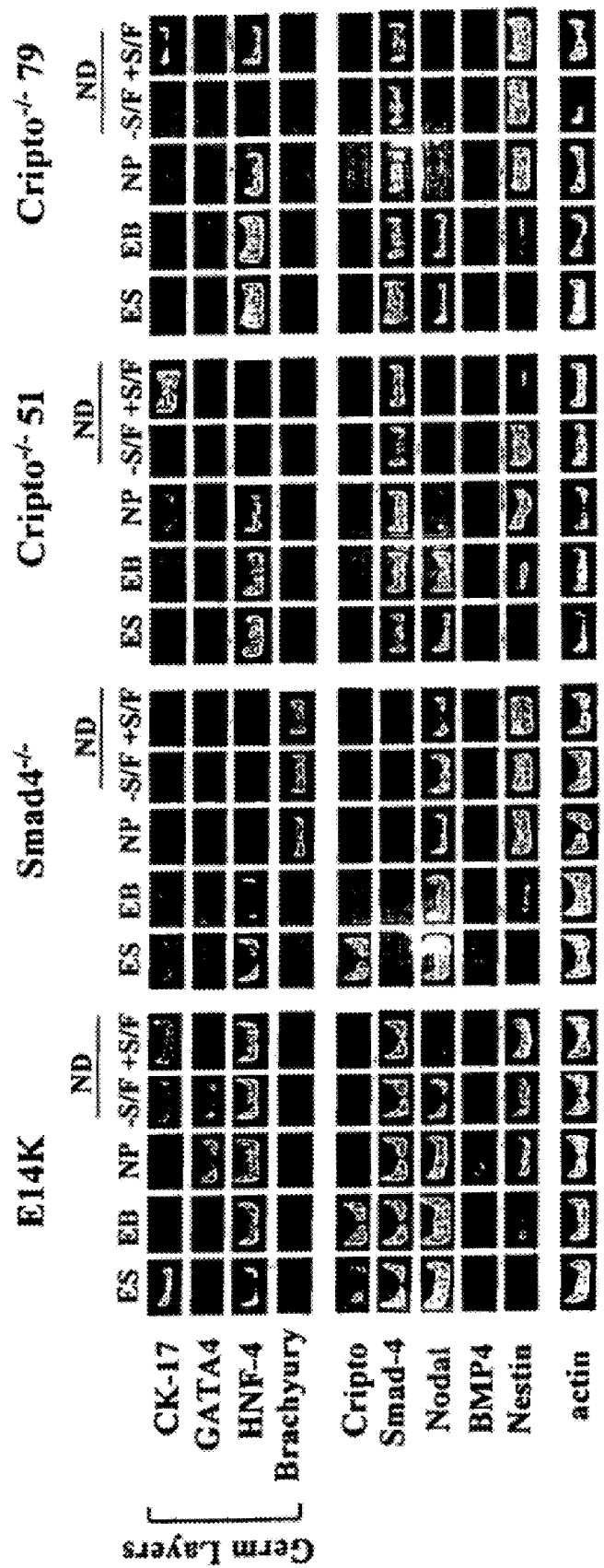
FIG. 3 is a series of photomicrographs showing the gene expression profile of germ layer cell markers, TGF-β signaling pathway members, and nestin, a marker of neural precursor cells, in in vitro differentiated E14K (parental line), Smad4$^{-/-}$, and two Cripto$^{-/-}$ ES cell lines. ES=embryonic stem cells; EB=embryoid bodies; NP=selection of neuronal precursors; ND=neuronal differentiation. −S/F=cultured without serum and growth factors; and +S/F=cultured in the presence of serum and growth factors.

Gene Expression Profiles of In Vitro Differentiated Smad4$^{-/-}$ and Cripto$^{-/-}$ Embryonic Stem Cells During embryogenesis, mutation of Smad and Cripto negatively influences mesodermal and epidermal cell development. Therefore, we analyzed the expression of several marker genes that are related to germ-layer formation such as the early endodermal transcription factor GATA4, the late endodermal factor hepatic nuclear factor 4 (HNF4) and the mesodermal marker Brachyury (FIG. 3). The Smad4$^{-/-}$ and Cripto$^{-/-}$ ES cells were in vitro differentiated to determine their differentiation capacities. Differentiation was performed using a five stages differentiation protocol (Lee et al., 2000; Chung et al., 2002) and analyzed gene expression profiles by semi-quantitative RT-PCR at various stages of cell development.

The Smad4$^{-/-}$ ES cells expressed no GATA4, a down-regulated HNF4 and an up-regulated Brachyury gene expression at late stages (NP and ND) of cell differentiation when compared to the parental E14K cell line (FIG. 3). The Cripto$^{-/-}$ cells had a down-regulation of GATA4 and an early (ES, EB, NP), but not late (ND) increase in HNF-4 transcription when compared to the WT TC1 cell line (FIG. 3). Interestingly, there was no late (ND) Brachyury expression in the Cripto$^{-/-}$ cells as seen in the TC1 cells. These data indicate that Smad4$^{-/-}$ cells developed early mesoderm at late stages of in vitro differentiation. Thus, treatment of PD using in vitro differentiated Smad4$^{-/-}$ ES cells may be most effective if the cells are transplanted at a relatively early stage (i.e., EB or NP).

We also determined the expression profile of the Smad4 and Cripto genes during ES cell differentiation. We found that Smad4 was constitutively expressed through all 5 stages of in vitro differentiation in both WT TC1 and the Cripto$^{-/-}$ cell lines (FIG. 3); whereas, Cripto expression appeared to be down-regulated at NP and ND stages in the WT E14K and Smad4$^{-/-}$ cells (FIG. 3). In all cell lines (WT and mutants) expression of Nodal, a TGF-β family member that interacts with Cripto, was highly upregulated early and downregulated late at cell development (FIG. 3).

Figure 4:
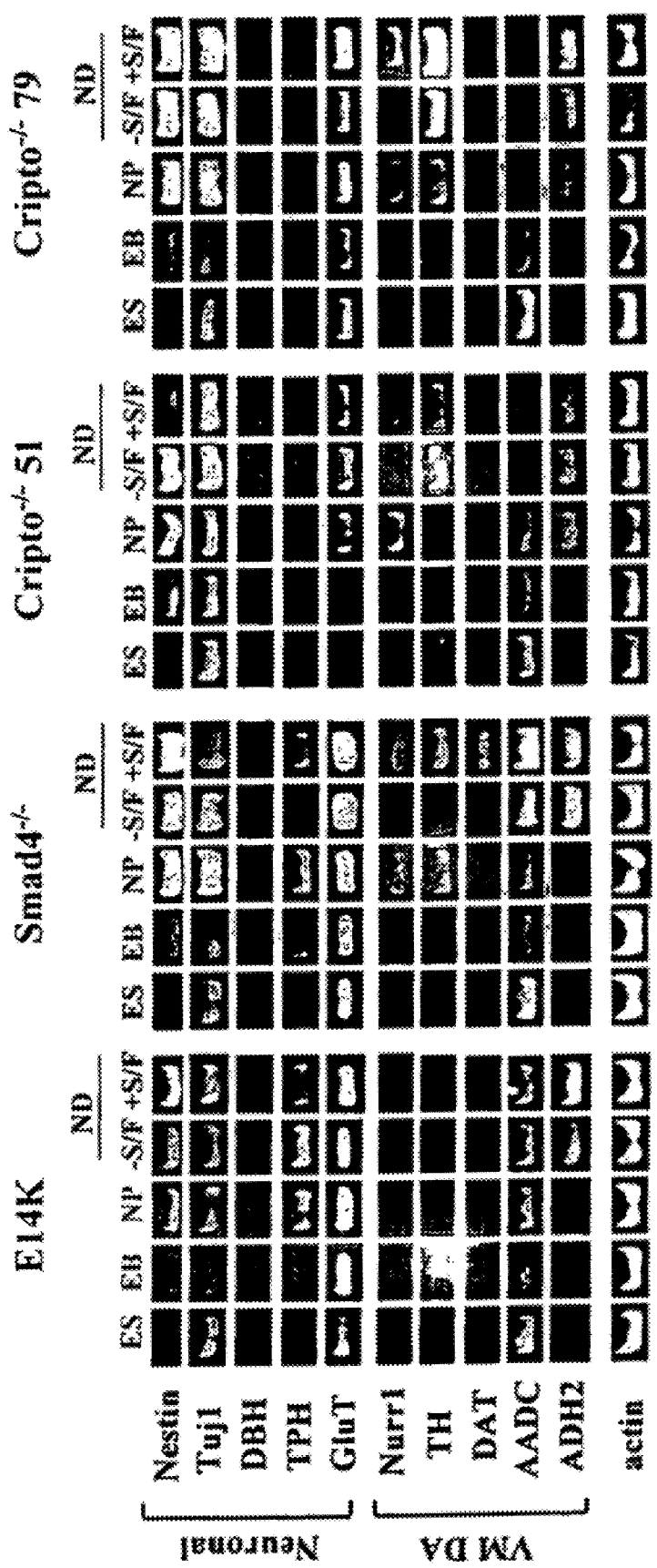
FIG. 4 is a series of photomicrographs showing the gene expression profile of general neuronal and dopaminergic cell markers in in vitro differentiated E14K (parental line), Smad4$^{-/-}$, and two Cripto$^{-/-}$ ES cell lines.

With the exception of the Brachyury mesodermal cell marker, differentiated the Smad4$^{-/-}$ cells progressively lost mesodermal markers (FIG. 3) compared to the WT ES cell line E14K. The differentiated Smad4$^{-/-}$ cells continued to express high levels of general neuronal and ventral mesencephalic markers, particularly dopaminergic markers (FIG. 4). Specifically, when compared to the WT ES cell line E14K, the Smad4$^{-/-}$ showed an increase of Tuj1 gene expression (a general neuronal marker) at the end of the neuronal precursor (NP; stage 3, day 8) and neuronal differentiation (ND; stage 5, day 15) stages (FIG. 4). Expression of the ventral mesencephalic dopaminergic markers TH, DAT, AADC, and Nurr-1 also steadily increased throughout the differentiation procedure. Of particular importance for the treatment of PD, expression of ADH2, an A9-specific marker, was also significantly increased during the later stages of differentiation.

Generally, the Cripto$^{-/-}$ ES cells also demonstrated a steady decline and/or loss of mesodermal markers throughout differentiation with a concomitant increase in nestin and Tuj1, the general ventral mesencephalic dopaminergic markers TH, DAT, AADC, and Nurr-1 (FIGS. 3 and 4).

Figure 5:
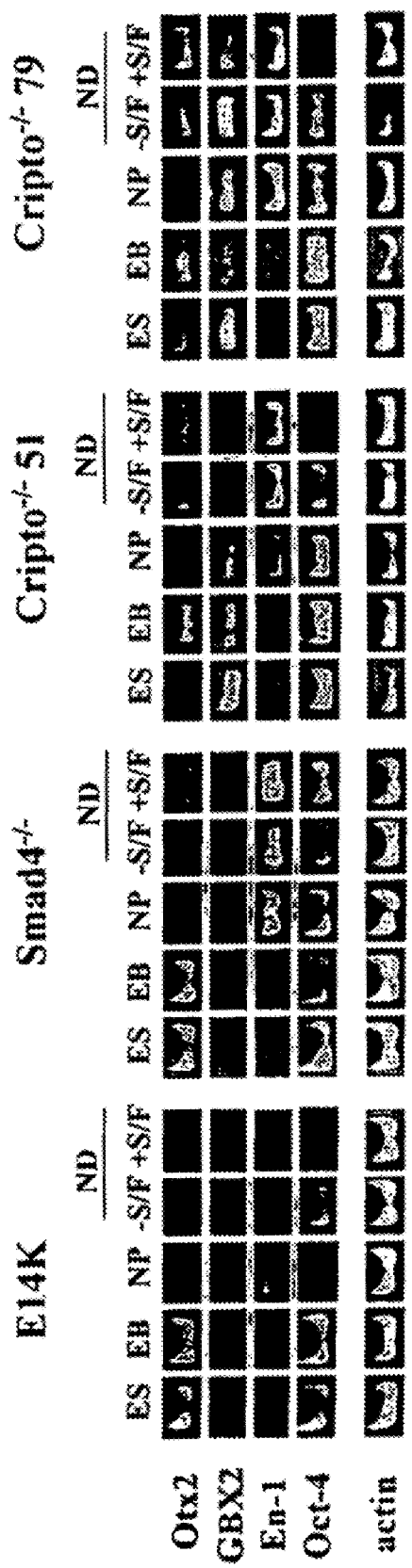
FIG. 5 is a series of photomicrographs showing the gene expression profile of markers known to be expressed in various regions of the developing brain in in vitro differentiated E14K (parental line), Smad4$^{-/-}$, and two Cripto$^{-/-}$ ES cell lines. Otx2 is a marker of forebrain and midbrain differentiation. GBX2 is a marker of hindbrain differentiation, En-1 is a transcription factor associated with dopaminergic differentiation.

Next, we analyzed the expression of transcription factors that play a developmental role at early embryonic stages within the midbrain-hindbrain territory and the ventral mesencephalon. We found that the gene expression profiles of the forebrain/midbrain marker Otx2 and the rostral hindbrain marker GBX2 was not different between the parent E14K and Smad4$^{-/-}$ cells (FIG. 5). Interestingly, analysis of the WT TC1 cell line revealed late expression of Otx2 and no expression of En-1, a transcription factor required for dopaminergic differentiation (FIG. 5). Otx2 and GBX2, however, were consistently up-regulated in the two Cripto$^{-/-}$ cell lines and En-1 was up-regulated in the NP and ND cell stages (FIG. 5). These data suggest that in vitro, Smad4$^{-/-}$ cells tended to express a more mid-brain gene profile, whereas the Cripto$^{-/-}$ cells expressed rostral CNS gene markers in addition to mid-brain phenotypes.

In Vitro Differentiation of Smad$^{-/-}$ and Cripto$^{-/-}$ ES Cells

The results from the RT-PCR experiments showed that the Smad4$^{-/-}$ and the Cripto79$^{-/-}$ had higher expression of the neuronal marker Tuj1 indicating an increase in neurogenesis. We, therefore, analyzed neuronal cell development after in vitro differentiation by immunocytochemistry. We found that both the WT and the mutant cell lines grew in Tuj1$^+$ cell clusters. In the parental ES cell line (E14K) the Tuj1$^+$ neurons were typically confined to small regions at the edge of these clusters. The density of Tuj1$^+$ neurons at these edge regions was 35.5+/−15.3 cells/field (n=23), whereas the center of the clusters had only few Tuj1$^+$ cells (1.2+/−1.3 cells/field, n=20). By contrast, the majority of the clusters in the corresponding Smad4$^{-/-}$ cultures contained Tuj1$^+$ neurons distributed within and around the clusters, with an average of 42.2+/−10.4 neurons/field (n=23). In the WT TC1 and the corresponding Cripto$^{-/-}$ cells, there was a mixed distribution of clusters with Tuj1$^+$ neurons in the periphery or in the center with no significant differences of amounts of Tuj1$^+$ neurons between the three cell lines. In addition to neuronal cell development all cell lines also developed GFAP$^+$ astrocytes.

We also performed immunocytochemistry experiments using the germ-layer markers myosin (mesodermal marker) and cytokeratin (CK; ectodermal and epidermal marker) after in vitro differentiation. CK$^+$ cell populations were present in all cell lines. Myosin-positive cells were present in the WT E14K and TC1 (59+/−2.9, n=20 and 97+/−4.9, n=20, respectively) and Smad4$^{-/-}$ cell lines (73+/−3.6, n=20), but were absent in the Cripto$^{-/-}$ cell cultures (none observed, n=40) indicating that the Cripto$^{-/-}$ ES cells were deprived to develop mesodermal cell populations in vitro. In addition, we analyzed the presence of immature cell types, such as Nestin$^+$ neural precursors and stage specific early antigen 1 (SSEA1)-positive immature stem cells. Both immature cell types were found in all cell cultures. Interestingly, there was a high proportion of SSEA1$^+$ cells in the Cripto$^{-/-}$ cell cultures (704+/−35.2, n=20), when compared to the corresponding WT TC1 cultures (1+/−0.3, n=40).

EXAMPLE 2

Transplantation of Cultured Smad4$^{-/-}$ and Cripto$^{-/-}$ Embryonic Stem Cells into the Mammalian Brain Preparation of ES Cells for Transplantation ES cells were cultured for four days in the absence of LIF on 100 mm Fisher brand bacteriological grade petri dishes to form embryoid bodies (EB). EBs were then transferred to 15 ml sterile culture tubes, spun at 1000 rpm for 5 min, and rinsed once in Ca$^{2+}$ and Mg$^{2+}$-free Dulbecco's Phosphate-Buffered Saline (D-PBS, Gibco/BRL). After rinsing, D-PBS was removed and 1.5 ml of trypsin solution was added. The cells were incubated for 5 minutes at 37° C. and triturated with fire polished Pasteur pipettes with decreasing aperture size to fully dissociate the cells. Finally, ES cells were spun at 1000 for 5 min and the trypsin solution replaced with 200 μl culture media. The viability and concentration of the ES cells was determined using a hemocytometer after staining with acridine orange and ethidium bromide.

Transplantation of Cultured ES Cells into Mice.

C57BL6 mice (25 g; Charles River, Wilmington, Mass.) were anesthetized with an i.m injection of a mixture of ketamine (100 mg/kg, Ketaset, Fort Dodge, Iowa) and xylazine (5 mg/kg, Xyla-Ject, Phoenix Pharmaceuticals, St. Joseph, Mo.), and placed in a Kopf stereotaxic frame (David Kopf Instruments, Tujunga, Calif.) equipped with a mouse adapter. Each animal received an injection of 1.0 µl (0.25 µl/min) ES cell suspension into the striatum (from Bregma: A+ 1.0 mm, L−/+1.8 mm, V-2.8 mm) using a 26-gauge, 10 µl Hamilton syringe. The ES cells were allowed to settle for two minutes after injection before the needle was removed. After surgery, each animal received an intraperitoneal (i.p) injection of Buprenorphine (0.032 mg kg) as postoperative anesthesia.

Histological Procedures

Four weeks after the implantation of ES cells, animals were terminally anesthetized by an i.p injection of pentobarbita (100 mg/kg) and perfused intracardially with 70 ml heparin saline (0.1% heparin 0.9% saline followed by 100 ml paraformaldehyde (4% in PBS). The brains were removed and post-fixed for 8 hours in the same 4% paraformaldehyde solution. Following post-fixation, brains were equilibrated in sucrose (20% in PBS), sectioned (40 µm) on a freezing microtome, and collected in PBS.

Immunohistochemistry

Sections were rinsed for 3×10 minutes in PBS, preincubated in 4% normal donkey serum (NBS; Jackson Immunoresearch Laboratory) for 60 minutes and then incubated overnight at room temperature with primary antibody diluted in PBS with 2% NGS and 0.1% Triton X-100. After additional rinsing 3×10 minutes in PBS the sections were incubated in fluorescent labeled secondary antibodies (Cy2/Rhodamine Red-X/Cy5 labeled, raised in donkey; Jackson Immunoresearch Laboratory) in PBS with 2% NGS and 0.1% Triton X-100 for 60 minutes at room temperature. After rinsing 3×10 minutes in PBS, sections were mounted onto gelatin coated slides and coverslipped in Gel/Mount (Biømeda Corp. CA USA).

Graft Analyses

Design based stereology was performed on the grafts using an integrated epifluorescent Axioskop-2 microscope (Carl Zeiss) and Stereo Investigator workstation (MicroBright-Field, Williston, Vt.). Graft volumes were calculated using a Cavalieri estimator and the resultant coefficient of error estimate established data precision ($p<0.05$). Grafts were classified in small and large grafts according to their size relative to striatum (25 mm$^3$), whereby small grafts were smaller (<25 mm$^3$) and large grafts larger (>25 mm$^3$) than striatum. Estimation of cell components in grafts was performed using a semi-quantitative scoring system. Grafts were stained using immunohistochemistry, examined under the microscope and scored by two to three independent investigators using the following criteria: 0=no cells (0%), 1=very few (<5%), 2=distributed (5-20%), 3=regional (20-50%), 4=dominant (>50%).

Cell Counting and Statistical Analyses

Cell populations in ND stage of in vitro differentiation were counted at 63× magnification, using a Zeiss Axioplan I fluorescent microscope, in randomly selected fields (N=16 or more). The cultures were also monitored at lower magnification (10× or 20×) to observe general growth pattern. Grafts were analyzed at 40× magnification and cell components scored as described above. For statistical analysis, the Statview software was used for performing analysis of variance (ANOVA) with an alpha level of 0.01 to determine possible statistical differences between group means. When significant differences were found, post hoc analysis was performed using Fisher's PLSD (alpha=0.05).

In Vivo Differentiation of Smad$^{-/-}$ and Cripto$^{-/-}$ ES Cells

The in vitro differentiation experiments demonstrated that Cripto$^{-/-}$ cells, but not Smad4$^{-/-}$ ES cells were inhibited in mesodermal (myosin-positive) cell formation. We, therefore, analyzed the in vivo differentiation capacities of the Smad4$^{-/-}$, the Cripto$^{-/-}$, and the WT E14K ES cells by transplanting 50,000 cells into the striatum of naïve animals and analyzing the grafts four weeks after transplantation. Both the WT and the mutant cells developed into either large or small graft sizes (40%, 52% and 23.5% large grafts; 35%, 29% and 23.5% small grafts; 25%, 19% and 53% no grafts for WT, Smad4$^{-/-}$ and Cripto$^{-/-}$ ES cells, respectively). Interestingly, stereology analyses revealed that smaller WT, Smad$^{-/-}$ and Cripto$^{-/-}$ grafts had a higher proportion of neuronal components (81.0+/−15.1, 91.2+/−6.0, and 97.1+/−4.0% neuronal graft component, respectively) when compared with corresponding larger surviving grafts (61.5+/−27.2, 69.3+/−25.8, and 51.0+/−29.9% neuronal graft component, respectively). Notably, there was a trend towards higher amounts of neurons in small Smad$^{-/-}$ and Cripto$^{-/-}$ grafts when compared to WT grafts, but this was statistically not significant.

Preliminary morphological examination of the transplants indicated that a variety of non-neuronal cells had developed. Sections were, therefore, stained with the ecto-/epidermal marker CK and the mesoderm marker Myosin, and scored for the presence of these germ-layers (see material and methods for details). The principal germ layer in the small grafts of all three ES cell lines was neuronal and no cells from the other germ-layers were found. By contrast, all larger grafts had significant amounts of cells from ecto-/epidermal and mesodermal germ layers. To examine if there were remaining immature ES cells, we stained grafts with SSEA1. Clusters of SSEA1$^+$ cells were found in most grafts regardless of the ES cell source.

Figure 6:
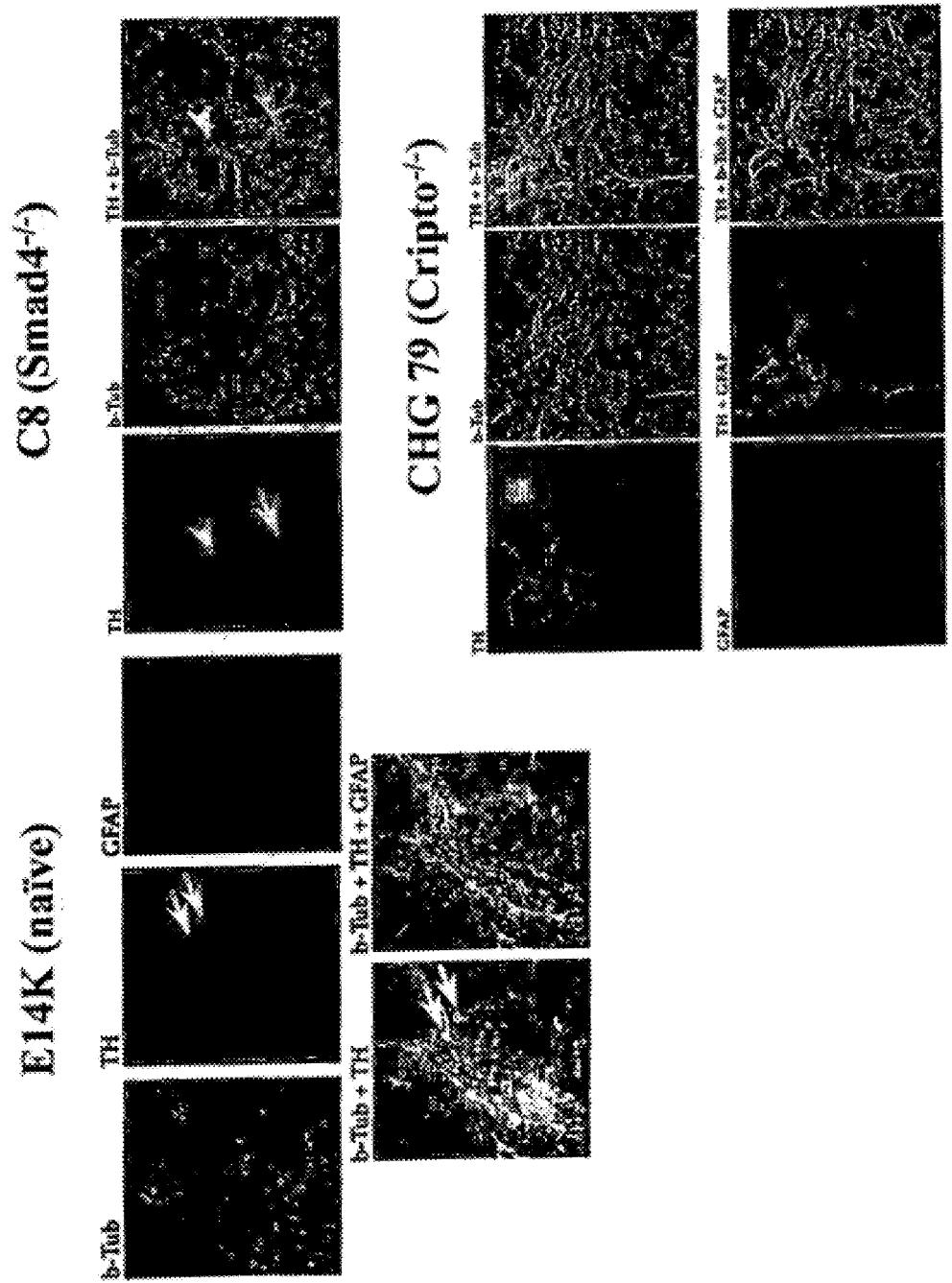
FIG. 6 is a series of photomicrographs of immunohistochemical staining of differentiated ES cell grafts four weeks after transplantation into the striatum of a naïve mouse.

Finally, we determined the presence of neuronal and glial cell markers in the grafts (FIG. 6). As shown in FIG. 4, β-tubulin strongly co-localizes with tyrosine hydroxylase but not with glial fibrillary acidic protein (GFAP), an astrocytic marker. These results clearly demonstrate that neurons differentiating from ES cell grafts lacking a TGF-β family member differentiate into dopaminergic neurons.

Inhibition of a TGF-β Family Member in Pluripotent Cells Expressing a Cell Fate-inducing Polypeptide These results demonstrate that the inhibition of a TGF-β family member (e.g., Smad4 or Cripto) alone can induce pluripotent cells, such as ES cells, to differentiate along a dopaminergic lineage. Furthermore, a significant proportion of the resulting dopaminergic neurons adopt A9-like phenotypic markers, making them highly desirable for transplantation into the brain of a PD patient.

The methods described above are applied to ES cells that overexpress one or more cell fate-inducing genes (e.g., Nurr-1 and PTX3). ES cells that overexpress such genes are well known in the art (see, for example, Wagner et al. *Nat. Biotechnol.* 17: 653-659, 1999; Chung et al. *Eur. J. Neurosci.* 16: 1829-1839, 2002; Kim et al. *Nature* 418: 50-56, 2002; U.S. patent application Ser. Nos. 09/626,677, filed Jul. 27, 2000, and 09/917,126, filed Jul. 27, 2001; hereby incorporated by reference). The combination of elevated levels of a cell fate-inducing gene and the inhibition of a TGF-β family member will result in ES cell differentiation is dopaminergic neurons, and specifically A9 neurons, in higher proportions produced from ES cells can be increased by overexpressing one or more cell-fate inducing genes (e.g., Nurr-1 and PTX3) in addition to inhibiting a TGF-β signaling pathway. This combination will result in a greater proportion of cultured ES cells differentiating into dopaminergic neurons and, specifically, neurons having an A9 phenotype.

Other Embodiments

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for generating dopaminergic neurons in vitro comprising the steps of:
   (i) providing pluripotent cells;
   (ii) inhibiting Smad4 in said pluripotent cells; and
   (iii) overexpressing a Nurr-1 polypeptide in said cells; and
   (iv) culturing said cells in vitro to produce dopaminergic neurons.

2. The method of claim 1, wherein PTX3 is overexpressed in said cells.

3. The method of claim 1, wherein Nurr-1 is overexpressed by:
   (i) providing a polynucleotide encoding said cell fate-inducing polypeptide operably linked to a promoter; and
   (ii) introducing said polynucleotide into said pluripotent cells under conditions suitable for expression of said polynucleotide.

4. The method of claim 1, wherein said pluripotent cells are human pluripotent cells.

5. The method of claim 1, wherein said pluripotent cells are mouse, rat, porcine, or non-human primate pluripotent cells.

6. The method of claim 4, wherein said pluripotent cells are embryonic stem cells.

7. The method of claims 1, wherein said dopaminergic neurons express a phenotype of A9 dopaminergic neurons.

8. The method of claim 1, wherein said Smad4 is inhibited by gene knockout of the nucleic acid encoding Smad4.

9. The method of claim 1, wherein said Smad4 is inhibited by overexpressing small interfering RNA complementary to the mRNA encoding Smad4 in said pluripotent cells.

10. The method of claim 1, wherein said Smad4 is inhibited by overexpressing antisense oligonucleotide of the nucleic acid encoding Smad4 in said pluripotent cells.

11. The method of claim 1, wherein said Smad4 is inhibited by contacting said pluripotent cells with antibodies that specifically bind to Smad4.

12. The method of claim 1, wherein said Smad4 is inhibited by overexpressing a dominant negative version of Smad4 in said pluripotent cells.

* * * * *